United States Patent [19]
Forouhi et al.

[11] Patent Number: 4,905,170
[45] Date of Patent: Feb. 27, 1990

[54] METHOD AND APPARATUS OF DETERMINING OPTICAL CONSTANTS OF AMORPHOUS SEMICONDUCTORS AND DIELECTRICS

[76] Inventors: Abdul R. Forouhi; Iris L. Bloomer, both of 7216 Clarendon St., San Jose, Calif. 95129

[21] Appl. No.: 224,559

[22] Filed: Jul. 26, 1988

Related U.S. Application Data

[63] Continuation-in-part of Ser. No. 119,855, Nov. 12, 1987.

[51] Int. Cl.$^4$ ............................................. G01N 21/00
[52] U.S. Cl. .................................... 364/556; 356/381
[58] Field of Search ............... 364/556, 498, 497, 496, 364/563, 526, 525; 356/381, 382, 128; 250/339, 341; 324/96

[56] References Cited

U.S. PATENT DOCUMENTS

| Re. 29,138 | 2/1976 | Dill et al. | |
| 3,892,490 | 7/1975 | Uetsuki et al. | |
| 4,335,961 | 6/1982 | Chou et al. | 356/361 |
| 4,498,772 | 2/1985 | Jastrzebski et al. | 356/357 |
| 4,555,767 | 11/1985 | Case et al. | 364/563 |
| 4,679,946 | 7/1987 | Rosencwaig et al. | 374/5 |
| 4,707,611 | 11/1987 | Southwell | 250/560 |
| 4,787,749 | 11/1988 | Ban et al. | 356/381 |

OTHER PUBLICATIONS

Forouhi & Bloomer, "Optical Dispersion Relations for Amorphous Semiconductors and Amorphous Dielectrics", Physical Review B, vol. 34, No. 10, Nov. 15, 1986.
Konova and Borissov, "Determination of Film Thickness . . . Angular Modulation in Reflection", Thin Solid Films 5/75, pp. 83–87.
E. E. Khawaja, "The Determination . . . Refractive Index and Thickness of a Transparent Film", J. Phys. D: Appl. Phys., vol. 9, 1976, pp. 1939–1943.
Ruiz-Urbietta et al., "Methods in Film Thickness and Optical Constants of Films and Substrates", Journal of the Optical Society of America, vol. 61, #3 (Mar. 1971), pp. 351–359.

Primary Examiner—Parshotam S. Lall
Assistant Examiner—S. A. Melnick
Attorney, Agent, or Firm—Fliesler, Dubb, Meyer & Lovejoy

[57] ABSTRACT

Disclosed is a method of and apparatus for determining the optical constants of materials in general and also for determining thicknesses of thin films. A complex index of refraction is derived that provides excellent fits to the measured n and k values of a large number of materials (including semiconductors, dielectrics, and metals) over a wide range of photon energies covering almost the entire range of the spectrum of electromagnetic radiation, including infrared, visible and ultraviolet.

23 Claims, 17 Drawing Sheets

METHOD AND APPARATUS OF DETERMINING OPTICAL CONSTANTS OF AMORPHOUS SEMICONDUCTORS AND DIELECTRICS

CROSS REFERENCE

This application is a continuation-in-part of the prior application:
Ser. No.: 07/119,855
Filing Date: Nov. 12, 1987
Inventors: A. Rahim Forouhi Iris L. Bloomer

FIELD OF INVENTION

The present invention generally relates to optical properties of materials, and more particularly, to methods and apparatus of determination of optical constants of materials as well as determination of thicknesses of thin films.

BACKGROUND OF THE INVENTION

Optical properties of any material can be described by the complex index of refraction, $N = n - ik$, or the complex dielectric function, $\epsilon = \epsilon_1 - i\epsilon_2$. $\epsilon$ is related to N by $\epsilon = N^2$, so that $\epsilon_1$ and $\epsilon_2$ can be determined from a knowledge of n and k: $\epsilon_1 = n^2 - k^2$ and $\epsilon_2 = 2nk$. The real and imaginary parts of the complex index of refraction, n and k, are termed refractive index and extinction coefficient respectively. In addition to k and $\epsilon_2$, which relate to absorption of light, the absorption coefficient, $\alpha = 2\omega k/c$, is used to describe absorption where $\omega$ represents photon frequency and c, the speed of light and where n and k, $\epsilon_1$ and $\epsilon_2$, and $\alpha$ are referred to as optical constants of the material. Values of optical constants depend on photon energy, $E = \omega$; that is, $N = N(E) = n(E) - ik(E)$, $\epsilon = \epsilon(E) = \epsilon_1(E) - i\epsilon_2(E)$, and $\alpha = \alpha(E)$. These functions are called optical dispersion relations.

Electrical properties of a material can be found from its optical properties. For example, a.c. conductivity, $\sigma$, is directly proportional to $\epsilon_2$, through $\sigma = E/h$ $\epsilon_2 = 2nkE/h$ where h is Planck's constant. Furthermore, d.c. conductivity, $\sigma_0$, is proportional to a time parameter, $\tau$, representing how long (on the average) an electron remains in the conduction band. This time parameter $\tau$ can be taken as the lifetime of the excited state to which the electron transfers due to optical (photon) absorption. Thus, $\sigma_0 = (N_f e^2 \tau)/m_e$ where $N_f$ is the number of free electrons per unit volume, e, the electron charge, and $m_e$, the electron mass.

In what follows, explicit consideration will be given to determination of n and k with the understanding that $\epsilon_1$ and $\epsilon_2$ can be obtained from this determination.

Previous formulations of optical dispersion relations vary for different materials, are complicated, and use different equations for different energy ranges. These previous formulations determine optical constants for semiconductors and dielectrics in closed analytical form only for a narrow range of photon energies just above the energy band gap, $E_g$, that is, for the absorption edge. In this range it is postulated that $\alpha$ as well as k and $\epsilon_2$ (since n is assumed constant for $E = E_g$) can be broken into two parts. For $\alpha < \alpha_0$ (where $\alpha_0$ represents some experimentally determined cut-off value), an empirical exponential dependence on E, referred to as Urbach's tail, is assumed. For $\alpha > \alpha_0$, a power law dependence on E is derived, based on a one electron model with infinite lifetime for the excited electron state. The value of the exponent depends on the type of transition: direct, forbidden, or indirect.

Beyond the absorption edge, optical constants are not determined in closed analytical form. Analysis of critical points in the Brillouin zone plays a major role in their determination. For example, an edge in the $\epsilon_2$ vs E spectrum is attributed to a transition corresponding to $\hbar\omega = E_{cv}(\vec{k}_{crit})$. At a critical point, $\vec{k} = \vec{k}_{crit}$, the function $E_{cv}(\vec{k}) = E_c(\vec{k}) - E_v(\vec{k})$ is an extremum. ($\vec{k}$ represents electron wave vector and indices c and v represent conduction and valence bands respectively.) A peak in $\epsilon_2$ vs E is attributed to a transition corresponding to an accidental pairing of two critical points occurring near the same energy (sometimes enhanced by exciton interactions).

The principle of causality leads to a fundamental relation between the real, n(E), and imaginary, k(E), parts of N(E), the Kramers-Kronig relation. Thus, theoretically, when k as a function of E is known, n(E) can be determined. However, except for harmonic oscillator fits to the measured data, formulations of n(E) do not relate it to k(E). Instead, n(E) is determined empirically by fitting data to various model equations. Commonly used are Sellmeier type equations or equations involving a sum of Sellmeier terms, all valid for a limited range of energies. The particular equation applied to a given material is determined by the resulting fit it gives to measured data.

When an oscillator fit is used, n can be related to k through the Kramers-Kronig relation. However, k cannot be correctly described at the absorption edge since the energy band gap is not incorporated into an oscillator model. In addition, many fitting parameters are required. For example, 22 parameters are used to describe n and k for crystalline Si in the 0 to 10 eV range.

For metals, two major interactions are commonly used to account for their optical properties. In the far and near infrared regime, a classical free electron-electromagnetic interaction is used, that is, the Drude free electron model. In the fundamental optical regime, quantum mechanical absorption of photons accounts for the interaction.

The low energy classical free electron model seldom agrees precisely with experiment. It is often found that the measured conductivity is less than the predicted classical value and that the current density and electric field are not in phase so that Ohm's law is not obeyed in the optical interactions. Also, some structure can be discerned in the optical constants. Furthermore, the Hagens-Ruben relation is violated in many instances with $n > k$ for very low energies. Several factors are held responsible for these discrepancies. One factor involves the anomalous skin effect whereby electrons near the surface have frequent collisions and therefore a shorter mean free path and smaller effective relaxation time that electrons deeper in the metal. Since the electromagnetic waves penetrate only a very short distance in the metal, they only interact with surface electrons. A second reason for disagreement is ascribed to bound electron transitions which influence the optical properties and yet do not provide any electrical conductivity. A third reason is attributed to multiple frequency dependent relaxation times for free electrons.

In the fundamental optical regime (where structure in optical constants is apparent for most materials), quantum mechanical absorption of photons accounts for the interaction. Two different quantum approximations can be found. The one-electron model approximates each electron as an independent particle where the random phase approximation takes into account the electron-electron interaction. An infinite lifetime of the excited state to which an electron transfers via photon absorption is mostly assumed in these approximations. Some treatments, however, do incorporate an interband relaxation time parameter in the expression for $\epsilon$. Formulations stemming from these approximations provide structural details for $\epsilon_2(E)$ such as thresholds, edges, peaks and saddle points through analysis of critical points of the Brillouin zone. These treatments, however, do not provide an analytical expression for $\epsilon_2(E)$ (or k(E)) applicable throughout the optical regime and thus cannot give $\epsilon_1(E)$ (or n(E)) as stipulated by the Kramers-Kronig relations. $\epsilon_1(E)$ (as well as n(E)) are treated from a phenomenological point of view. Moreover, they do not resolve the issue of direct transitions (in which electron momentum is conserved), versus indirect transitions (where phonons are absorbed or emitted in order to conserve momentum) in metals.

Currently, there are several methods to determine the optical constants of a medium (bulk and thin film). See, e.g., "*Handbook of Optical Constants of Solids*", edited by E. D. Palik (Academic Press, N.Y., 1985), and O. S. Heavens, in "*Physics of Thin Films*", Vol. 2, edited by G. Hass and R. E. Thun (Academic Press, N.Y., 1964), for reviews of various methods. These methods of determining n and k, however, are complicated and at times yield inaccurate results.

For bulk materials, a widely used method of determining n and k is by Kramers-Kronig (K-K) analysis of the reflectance spectrum. Reflectance, R, is defined as the ratio of the intensity of the reflected beam, $I_R$, to that of the incident beam, I, that is, $R = I_R/I$. In principle, optical constants of bulk materials as functions of energy can be determined by K-K analysis if R(E) is known for all energies from zero to infinity (0 to $\infty$). In practice, however, R is measured only over a limited range of energies and extrapolated beyond the range of measurements. These extrapolations introduce errors in determination of the optical constants. In addition, although there are different schemes to extrapolate R to infinity, they are intrinsically flawed because they all assume $R(\infty)=0$. This is because in classical theory of dipersion it is assumed that $n(\infty)=1$ and $k(\infty)=0$, which implies that $R(\infty)=0$; whereas, as described later, it is shown that $n(\infty)\neq 1$ and $k(\infty)\neq 1$, which implies that $R(\infty)\neq 0$.

Another method of determining the optical constants of a medium is by ellipsometry. In this method, n and k are determined by measuring the change in the state of polarization of reflected light. Ellipsometry requires complex instrumentation, and needs certain sophistication in interpretation of the measurements. Moreover, alignment of the polarizing elements is very important and can lead to errors. In addition, ellipsometry is rarely carried out at energies above 6 eV for lack of effective polarizing elements.

For thin films, n and k at each wavelength are currently determined from two independent measurements made at those wavelengths, such as the reflectance R and transmittance T of the same film (RT method), or transmittance of two films of different thicknesses (TT method). (Transmittance is defined as the ratio of transmitted to incident intensity.) In all these cases, the thickness of the film must be determined by other means. A disadvantage of the RT method is that the substrate upon which the film is deposited must be transparent in order to make the transmittance measurement possible. This limits the choice of substrate for deposition of thin films. (Note that properties and growth rates of thin films can be significantly altered depending on the type of substrate. In fact, the dependence of the film properties on the type of substrate is sometimes used for selective deposition of thin films.) An obvious disadvantage of the TT method, that is, using two films of different thicknesses for determination of the optical constant, is that the method assumes no variation of the optical constants with thickness, which is not usually the case.

It is an object of the present invention to provide a simple and accurate method and apparatus for determining the optical constants of materials based on new expressions for n and k. It is another object of the present invention to provide a method and apparatus of determining simultaneously the optical constants and the thicknesses of thin films.

A further object of the present invention is to determine a.c. and d.c. conductivity for materials.

SUMMARY OF THE INVENTION

The present invention, based on quantum theory of absorption of photons, presents an accurate and convenient method and apparatus of determining the optical constants of materials in general as well as optical constants and thicknesses of thin films.

In this patent application, a new method is presented for determining the complex index of refraction of materials. An expression for k(E) based on a one-electron model is employed and the need to invoke an accidental degeneracy of two critical points in order to account for peaks is eliminated. A peak in the k vs E spectrum can be attributed to a transition corresponding to $\hbar\omega = E_c(\vec{k}_{crit}) - E_v(\vec{k}_{crit})$. The value of n(E) is derived from k(E) via the Kramers-Kronig relation. The value of n(E) is determined to approach a value greater than one in the limit as E approaches infinity, in contrast to the classical theory of dispersion where $n(\infty)$ is determined to equal 1.

The resulting expressions simultaneously provide excellent fits to the measured and published n and k values of a large number of materials (including conductors, dielectrics, metals, and liquids) over a wide range of photon energies covering almost the entire range of the spectrum of elcetromagnetic radiation, including infrared, visible and ultra violet with far fewer parameters (all of which have physical significance) than other methods.

When other optical constants such as $\epsilon_1 = n^2 - k^2$ and $\epsilon_2 = 2nk$, as well as normal-incidence reflectance, $R = [(n-1)^2 + k^2]/[(n+1)^2 + k^2]$, are expressed in terms of these new equations for k(E) and n(E), excellent fits to experimental data are obtained.

Other objects, features, and advantages of the present invention will become apparent upon consideration of the following detailed description and the accompanying drawings.

DETAILED DESCRIPTION OF THE INVENTION

Figure 2:
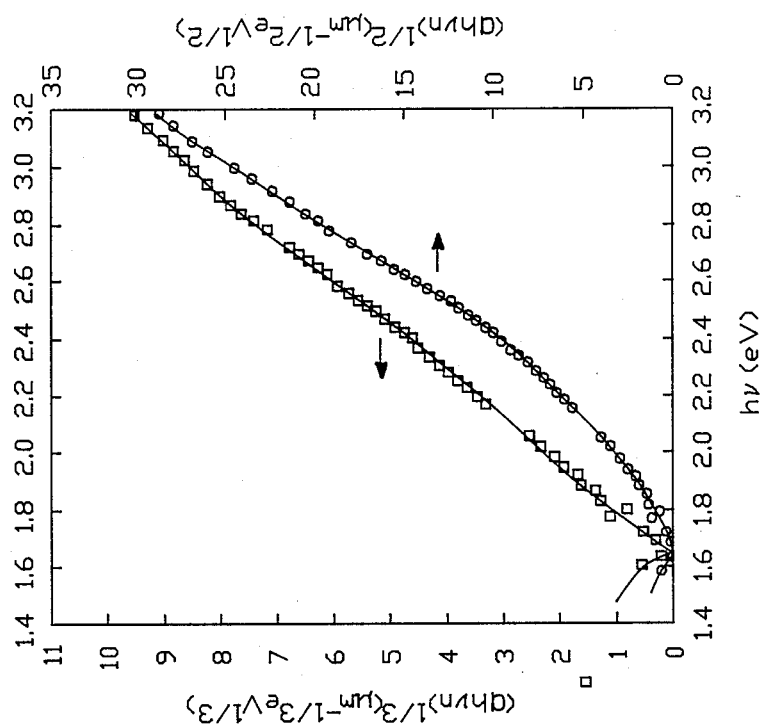
FIG. 2 shows the correspondence between the theoretical (solid lines) and the experimental data points. The experimental data point are from Klazes et al for a-Si produced by glow-discharge decomposition of SiH$_4$ (film number 3 of the original Klazes et al reference).

The objectives of this invention are achieved by measuring reflectance (or transmittance) using, for example, a spectrophotometer and then applying the formulae for n and k which are derived in the following manner.

I. Amorphous Semiconductors and Dielectrics

The probability for a transition per unit time, $W_{d\Omega}$ (due to photons contained within the solid angle $d\Omega$) between two arbitrary states, $|a>$ and $|b>$, where $E_b > E_a$ is examined. From first order time dependent perturbation theory, $$d\Omega = (\pi e^2/m_e)(n_{\omega,l}/\omega)|<b|\vec{P}\cdot\vec{\epsilon}^{(l)}|a>|^2 \rho_{\omega,d\Omega}.\quad \text{Eq.(1)}$$

where e, $m_e$, and $\vec{P}$ are the electron charge, mass, and momentum and $n_{\omega,l}$ represents the occupation number for photons with angular frequency $\omega$ and polarization vector $\vec{\epsilon}^{(l)}$ (l=1, 2 corresponding to two possible polarization states). The term $\rho_{\omega,d\Omega}d\omega$ gives the number of allowed photon states in the frequency range $\omega$ to $\omega+d\omega$ as follows.

$$\rho_{\omega,d\Omega}d\omega = (\kappa^2)(d\kappa)d\Omega/(2\pi)^3 = \omega^2 d\Omega(2\pi c)^3 d\omega \quad \text{Eq.(2)}$$

Eq.(1) holds only if $E_b - E_a = \hbar\omega$. The momentum matrix element in Eq.(1) can be replaced by the position matrix element since $<b|\vec{P}|a> = im_e\omega<b|\vec{x}|a>$. Furthermore, the incident intensity, $I_0(\omega)$, can be substituted in Eq.(1) since $$I_0(\omega)d\omega = n_{\omega,l}c\hbar\omega\rho_{\omega,d\Omega}d\omega = \frac{\hbar\omega^3 n_{\omega,l}d\Omega}{8\Pi^3 c^2}d\omega. \quad \text{Eq. (3)}$$

In terms of these parameters, the transition probability rate W is $$W = (8\pi^2/3\hbar^2 c)(e^2 I_0)|<b|x|a>|^2 \quad \text{Eq.(4)}$$

where the two independent directions of polarization, $\vec{\epsilon}^{(1)}$ and $\vec{\epsilon}^{(2)}$, have been summed over and an integration over all propagation directions, $d\Omega$, has been performed.

The energy absorbed per unit time, $S(\omega)$, is obtained by multiplying Eq.(4) by a $\hbar\omega$ as follows:

$$S(\omega) = (8\pi^2/3\hbar c)(e^2\omega I_0)|<b|x|a>|^2 \quad \text{Eq.(5)}$$

Eq.(5) holds only if the excited state $|b>$ has an infinite lifetime. If the excited state $|b>$ has a finite lifetime, $\tau$, according to first order time dependent perturbation theory, the absorption probability contains a damping factor as follows:

$$(\hbar^2\gamma/2\pi)(1/((E_b - E_a - \hbar\omega)^2 + \hbar^2\gamma^2/4) \quad \text{Eq. (6)}$$

where $\gamma = 1/\tau$. Then, the energy absorbed in the frequency range $\omega$ to $\omega+d\omega$ per unit time, $\Phi(\omega)d\omega$, contains this factor:

$$\Phi(\omega)d\omega = \quad \text{Eq. (7)}$$

$$S(\hbar^2\gamma/2\pi)(1/((E_b - E_a - \hbar\omega)^2 + \hbar^2\gamma^2/4)d\omega$$

Note, in the limit $\gamma \to 0$, $$(\hbar^2\gamma/2\Pi)(1/((E_b - E_a - \hbar\omega)^2 + \hbar^2\gamma^2/4) \to \delta(E_b - E_a - \hbar\omega)$$

so that $\lim \int \Phi(\omega)d(\hbar\omega) = S(\omega)$ where $\omega = \dfrac{E_b - E_a}{\hbar}$.

The absorption coefficient $l(\omega)$ is then defined by $$l(\omega) = \lim_{\Delta x \to 0} (-1/I)\Delta I/\Delta x = (1/I_0)\theta\Phi \quad \text{Eq. (8)}$$

where $\theta$ represents the number of possible transitions per unit volume in a layer of thickness $\Delta x$. Since the extinction coefficient, k, is directly related to $l(\omega)$ by $$k = lc/2\omega, \quad \text{Eq.(9)}$$

from Eqs.(7), (8) and (9), k is then determined to be $$k = (\theta 2\pi/3)e^2\hbar \; |<b|\vec{x}|a>|^2 (\gamma/((E_b - E_a - \hbar\omega)^2 + (\hbar^2\gamma^2)/4) \quad \text{Eq. (10)}$$

Eq.(10) is applied to the problem of absorption in amorphous semiconductors and dielectrics. In amorphous semiconductors and dielectrics short range order plays a key role in the absorption process. Locally, the electronic states of the amorphous solid may be considered to be a broadened superposition of molecular orbital states. For example, in tetrahedrally coordinated covalent materials, linear combinations of atomic orbitals lead to bonding ($|\sigma>$) and antibonding ($|\sigma^*>$) molecular states which then broaden into valence and conduction bands when the solid is formed.

As seen in Eq.(7), the maximum value for $\Phi$ occurs when $\omega = E_b - E_a$. In the following we will assume that maximum absorption occurs when $\hbar\omega = E_{\sigma^*} - E_{\sigma'}$ where $E_{\sigma^*}$ and $E_{\sigma'}$ are energies in the conduction and valence bands such that $E_{\sigma'} = E_\sigma^*$ and $E_{\sigma'} = E_\sigma$. This is consistent with the fact that the density of states in the conduction and valence bands is a maximum for $E_{\sigma^*}$ and $E_{\sigma'}$. If $E_b = E_{\sigma^*}$ and $E_a = E_{\sigma'}$, then $|b> = |\sigma'^*>$ and $|a> = |\sigma'>$.

In Eq.(10), $\theta$ is proportional to the number of possible transitions from the valence to the conduction band. Assuming a complete lack of momentum conservation, $\theta$ will depend on the number of occupied states in the valence band, $\hbar_v(E) f_v(E) dE$, and on the number of unoccupied states in the conduction band $\hbar_c(E')$ (1-f(E'))dE' which are separated by an energy $\omega$ from the states in the valence band. $\hbar_v(E)$ and $\hbar_c(E)$ represent the density of states in the valence and conduction band, and f(E) represents the Fermi function. Therefore, $$\theta \propto \int\int dE\, dE'\, \eta_v(E)\, f(E)\, \eta_c(E')(1 - f(E'))$$

$$\delta(E' - (E + \hbar\omega))$$

or $$\theta \propto \int \eta_v(E)\, f_v(E)\, \eta_c(E + \hbar 1)(1 - f_c(E + \hbar\omega))dE \quad \text{Eq. (12)}$$

For temperatures which are not too high, semiconductors are insulators, so that $f_v(E)$ is of order unity and $f_c(E + \omega)$ is of order zero. For this case $$\theta \propto \int_{E_{bottom} - \hbar\omega}^{E_{top}} \eta_v(E)\, \eta_c(E + \hbar\omega)\, dE \quad \text{Eq. (13)}$$

where $E_{top}$ represents the energy at the top of the valence band and $E_{bottom}$ represents the energy at the bottom of the conduction band so that the optical energy band gap, $E_g$, is given by:

$$E_g = E_{bottom} - E_{top} \quad \text{Eq. (14)}$$

Assuming density of states in the Valence and conduction bands can be expressed in terms of energy to some power, that is, $$\eta_v(E) = \text{const.}\, (E_{top} - E)^p$$

$$\eta_c(E) = \text{const.}\, (E - E_{bottom})^s$$

Eq.(13) can be evaluated as $$\theta = \text{const.}\, (\hbar\omega - E_g)^{p+s+1} \quad \text{Eq. (15)}$$

If the valence and conduction bands are parabolic so that $p = s = \frac{1}{2}$, $$\theta = \text{const.}\, (\hbar\omega - E_g)^2 \quad \text{Eq. (16)}$$

Assuming this is the case, the extinction coefficient is then determined from Eqs.(10) and (16) to be $$k = \quad \text{Eq. (17)}$$

$$\text{const.}(2\Pi/3)e^2\hbar^2|<\sigma'^*|x|\sigma'>|^2 \gamma/[(E_{\sigma'^*} - E_{\sigma'} - \hbar\omega)^2 + (\hbar^2\gamma^2)/4](\hbar\omega - E_g)^2$$

We can rewrite Eq.(17) in the following form:

$$k(E) = \frac{A(E - E_g)^2}{E^2 - BE + C}, \quad \text{Eq. (18)}$$

where $$A = \text{const.}(2\Pi/3)e^2\hbar^2|<\sigma'^*|\vec{x}|\sigma'>|^2 \gamma, \quad \text{Eq. (19)}$$

$$B = 2(E_{\sigma'^*} - E_{\sigma'}), \quad \text{Eq. (20)}$$

and $$C = (E_{\sigma'^*} - E_{\sigma'})^2 + (\hbar^2\gamma^2)/4. \quad \text{Eq. (21)}$$

It can be seen from Eqs.(19), (20), and (21) that $A>0$, $B>0$, $C>0$ and that $4C-B^2>0$. This relationship is important because n(E) cannot be determined from Kramers-Kronig analysis unless these conditions are met.

The two seemingly unrelated quantities n and k are related by Kramers-Kronig relations, also known as dispersion relations. These relations are a direct consequence of the analytic behavior of $N(E) = n(E) - ik(E)$. In turn, the analytic behavior of N(E) stems from the principle of causality, which states that no signals can be transmitted through a medium at a speed greater than that of light in vacuum.

A consequence of the analytical behavior of N(E) is that its real and imaginary parts are related by $$Re[N(E)] = 1/\pi\, P.V. \int_{-\infty}^{\infty} \{Im[N(E')]\}/(E' - E)\, dE', \quad \text{Eq. (22)}$$

provided N(E') vanishes at infinity. P.V. denotes Cauchy's principle value integral.

If N(E) tends to a constant at infinity, Eq.(22) must be replaced by $$Re[N(E) - N(\infty)] = \quad \text{Eq.(23)}$$

$$1/\pi\, P.V. \int_{-\infty}^{\infty} \{Im[N(E') - N(\infty)]\}/(E' - E)\, dE'$$

where $N(\infty) - \lim_{E\to\infty} N(E) = n(\infty) - ik(\infty)$

Thus, if the functional form of k(E) is known for all energies, then the functional form of n(E) for all energies can be determined.

Assuming Eq.(18) for k(E) holds, n(E) can be found from Eq.(23).

$$n(E) - n(\infty) = \quad \text{Eq.(24)}$$

$$1/\pi\, P.V. \int_{-\infty}^{\infty} [k(E') - k(\infty)]/(E' - E)\, dE'$$

Or substituting for k(E) given by Eq.(18) we get $$n(E) - n(\infty) = \quad \text{Eq.(25)}$$

$$1/\pi\, P.V. \int_{-\infty}^{\infty} \frac{A[(B - 2E)E' + E_g^2 - C]}{(E'^2 - BE' + C)(E' - E)}\, dE' = 1/\pi\, [-2\pi iR - \pi iS]$$

where R is the residue of the integrand at the pole located in the lower half of the complex E plane, and S is the residue evaluated at the pole located along the real axis.

The pole of the integrand of Eq.(25) in the lower half plane is at $B/2 - iQ$ where $Q = \frac{1}{2}(4C - B^2)^{\frac{1}{2}}$, and the pole along the real axis is at E. Thus, we obtain $$n(E) = n(\infty) + (B_0 E + C_0)/(E^2 - BE + C) \quad \text{Eq.(26)}$$

where $$B_0 = A/Q\, [-(B^2/2) + E_g B - E_g^2 + C] \quad \text{Eq.(27)}$$

-continued
and $$C_0 = A/Q \, [E_g^2 + C) \, B/2 - 2E_g C]. \quad \text{Eq.(28)}$$

It is expected that $N(E) - N(\infty)$ is analytic in the lower half of the complex E plane (rather than the upper half of the plane) because $N(E)$ is written as equal to $n(E) - ik(E)$ (rather than $n(E) + ik(E)$). Indeed, it can be shown that $$\begin{aligned} N(E) - N(\infty) &= [n(E) - n(\infty)] - i[k(E) - k(\infty)] \\ &= \frac{A}{Q} \frac{(B - 2E_g)(B/2 + iQ) + E_g^2 - C}{B/2 + iQ - E} \end{aligned} \quad \text{Eq.(29)}$$

which is analytic in the lower half of the complex E plane, since $Q > 0$.

It is usually assumed that $n(\infty)$ equals unity. Our results discussed below, however, indicate that $n(\infty) > 1$ (the exact value depending on the particular material). The above analysis therefore demonstrates that if $k(E)$ is given by equation (18), then five parameters, that is, $A$, $B$, $C$, $E_g$, and $n(\infty)$, are sufficient to fully describe the dependence of both n and k on e. Alternatively, energy dependence of both k and n given by Eqs.(18) and (26) can be fully and simultaneously determined if only four of the six parameters $E_g$, A, B, C, $B_0$, and $C_0$ ($B_0$ and $C_0$ are not independent parameters according to equations (27) and (28)), together with $n(\infty)$ are specified. In principle, therefore, both n and k as functions of E are simultaneously determined if altogether five values of n and k for specified energies are known, where at least one of which is a value for n. In practice, however, the scheme described below proves to be more useful.

Differentiating $k(E)$ with respect to E and setting $dk/dE$ equal to zero, we find that $k(E)$ has a minimum at $$E_{min} = E_g, \quad \text{Eq.(30)}$$

(where, of course, k evaluated at $E_g$, namely $k(E_g)$, equals zero), and a maximum at $E_{max}$ given by $$E_{max} = \frac{BE_g - 2C}{2E_g - B}. \quad \text{Eq.(31)}$$

The value of k evaluated at $E_{max}$, $k_{max}$, is then $$k_{max} = \frac{4A(E_g^2 - BE_g + C)}{4C - B^2} \quad \text{Eq.(32)}$$

Let us also assume that the value of k at an arbitrary point $E_{fit}$ (different from $E_g$ and $E_{max}$) is known and has a finite value equal to $k_{fit}$, namely, $$k_{fit} = \frac{A(E_{fit} - E_g)^2}{E_{fit}^2 - BE_{fit} + C}. \quad \text{Eq.(33)}$$

Simultaneous solution of Eqs.(30) through (33) yields $E_g$, A, B, and C in terms of $E_{min}$, $E_{max}$, $k_{max}$, and $k_{fit}$:

$$B = \frac{B_2 + (B_2^2 - 4A_2C_2)^{1/2}}{2A_2}, \quad \text{Eq.(34)}$$

-continued
where $$A_2 = (E_g - a)(E_{fit} - a) + L,$$

$$B_2 = (E_g - a)(E_{fit}^2 - b) + (E_{fit} - a)(E_g^2 - b) + 4La,$$

and $$C_2 = (E_g^2 - b)(E_{fit}^2 - b) + 4LB,$$

with $$a = \frac{E_{max} + E_g}{2},$$

$$b = E_g E_{max}, \text{ and } L = \frac{K_{max}(E_{fit} - E_g)^2}{4k_{fit}}.$$

After B is evaluated, C and A are then given by $$C = aB - b \quad \text{Eq.(35)}$$

and $$A = k_{fit}(E_{fit}^2 - BE_{fit} + C)(E_{fit} - E_g)^2. \quad \text{Eq.(36)}$$

Therefore, if $E_{min}$, $E_{max}$, $k_{max}$, and $k_{fit}$ are known, then $E_g$, A, B, and C are determined, and thus k as a function of E is completely defined. As discussed previously, n as a function of E can be determined from $k(E)$ and is given by Eq.(26), where $B_0$ and $C_0$ are evaluated through Eqs.(27) and (28). However, in order to specify $n(\infty)$ we must know the value of n at an arbitrary point $E'_{fit}$, that is, $n_{fit} = n(E'_{fit})$ must be known. Here, $E'_{fit}$ may or may not be equal to $E_{fit}$.

Examples For Amorphous Materials

As seen in FIGS. 1–8 and described below, the experimentally determined n and k of various amorphous semiconductor and dielectric thin films indeed obey dispersion relations given by equations (18) and (26). The parameters describing $n(E)$ and $k(E)$ for each example are given in FIG. 9.

1. (a-Si and a-Si:H)

Amorphous silicon (a-Si) and hydrogenated amorphous silicon (a-Si:H) semiconducting thin films are widely used in microelectronic devices, solar energy cells, optical media, and radiation detectors. Their optical and electrical properties have, therefore, been previously studied in detail. The measured optical constants, that is, n and k, over a wide range of energies, of a variety of a-Si and a-Si:H which were prepared by different methods under various process conditions are presented in books and numerous articles. These studies demonstrate that amorphous silicon and hydrogenated amorphous silicon films having different optical properties can be produced if preparation methods are changed. This is in contrast to, e.g., crystalline silicon where a unique set of data does, in principle, describe its optical properties.

Figure 1:
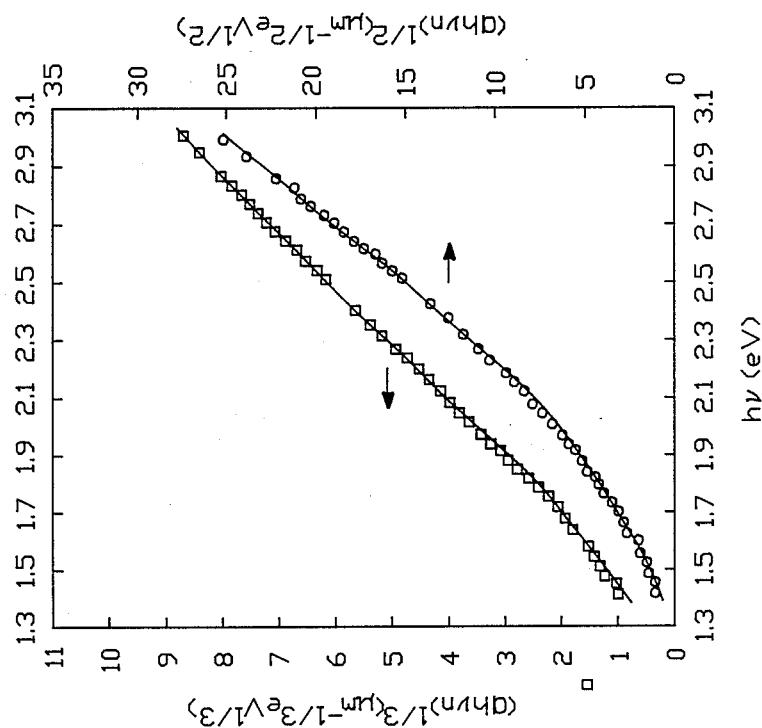
FIG. 1 shows the correspondence between the theoretical (solid lines) and the experimental data points for optical constants ($\alpha h\nu n$) versus energy ($h\nu$). The analytical form of n and k are given by equations (26) and (18) with the constants specified in FIG. 9. The experimental data points are from R. H. Klazes, M. H. L. M. van den Broek, J. Bezemer, and S. Radelaar, Philos. Mag. B 45, 377 (1982) for a-Si produced by sputtering of crystalline silicon in Ar/H$_2$ ambient (film number 2 of the original Klazes et al reference). (Solid lines in this FIG. 1 and in FIG. 2 represent plot of $(\alpha h\nu n)^{\frac{1}{2}}=(10.136 E^2 nk)^{\frac{1}{4}}$ and $(\alpha h\nu n)^{\frac{1}{3}}=(10.136 E^2 nk)^{\frac{1}{3}}$ versus $h\nu=E$.)

(i) Experimental data presented in FIGS. 1 and 2 are from Klazes et al, *Philos. Mag.* B45, 377 (1982). The films were produced by RF reactive sputtering of crystalline silicon in a mixture of argon and hydrogen, and by capacitance RF glow-discharge decomposition of silane (SiH4) diluted in argon. They were deposited on glass or fused silica substrates at deposition temperatures of 200° C. and 370° C. for sputtering and glow-discharge, respectively.

The optical constants were determined by measuring the spectral reflectance and transmittance of the film-substrate system at photon energies between 0.6 and 3.2 eV.

Although the films are presented as a-Si in the original reference, it may more appropriately be presented as a-Si:H, since films prepared by both sputtering in the presence of hydrogen and glow-discharge decomposition of SiH$_4$ would incorporate hydrogen in the film.

In FIGS. 1 and 2, (ahyn)$^{\frac{1}{2}}$ are plotted versus hy, where a denotes absorption coefficient given by a=(4pk)/g an hy denotes photon energy E. Klazes et al argued that (ahyn)$^{\frac{1}{3}}$ $\alpha$ (hy$-E_g$) provides a better fit to their experimental data than (ahyn)$^{\frac{1}{2}}$ $\alpha$ (hy$-E_g$), from which they deduced optical band gap $E_g$ using a linear extrapolation of (ahyn)$^{\frac{1}{3}}$ as a function of photon energy hy. However, as seen in FIGS. 1 and 2, a remarkably good fit was found between the experimental data and the corresponding theoretical curves, using formulae (18) and (26). The fit is such that the theoretical curves even pass smoothly through the two "apparently" misplaced data points at hy$\simeq$1.6 eV in FIG. 2.

Figure 3:
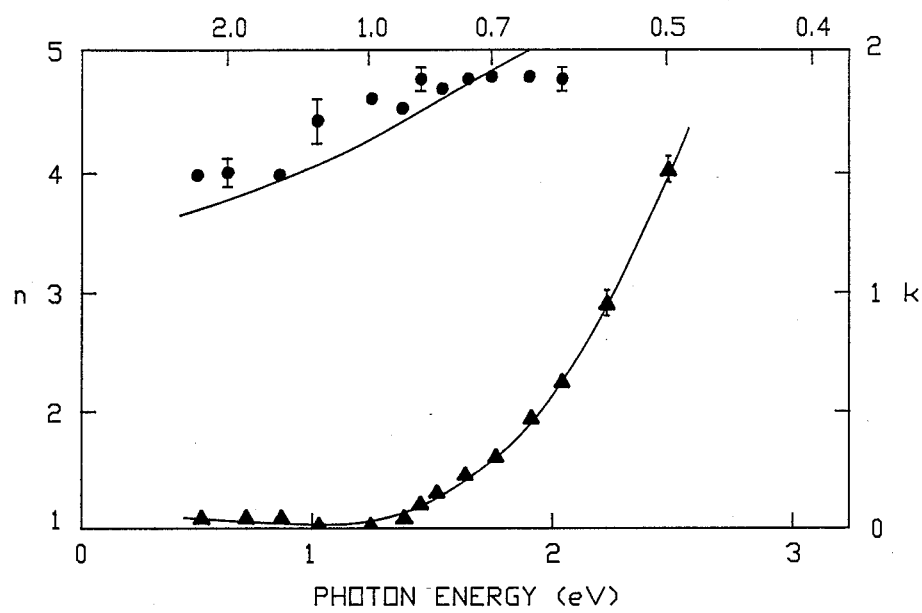
FIG. 3 shows the correspondence between the theoretical (solid lines) and the experimental data points. The experimental data points are from D. R. McKenzie, N. Savvides, R. C. McPhedran, L. C. Botten, and R. P. Netterfield, J. Phys, C 16, 4933 (1983), where the circle and triangle symbols represent n and k data points for a-Si produced by sputtering of crystalline silicon in Ar ambient (film number 1 of the original McKenzie et al reference).
Figure 4:
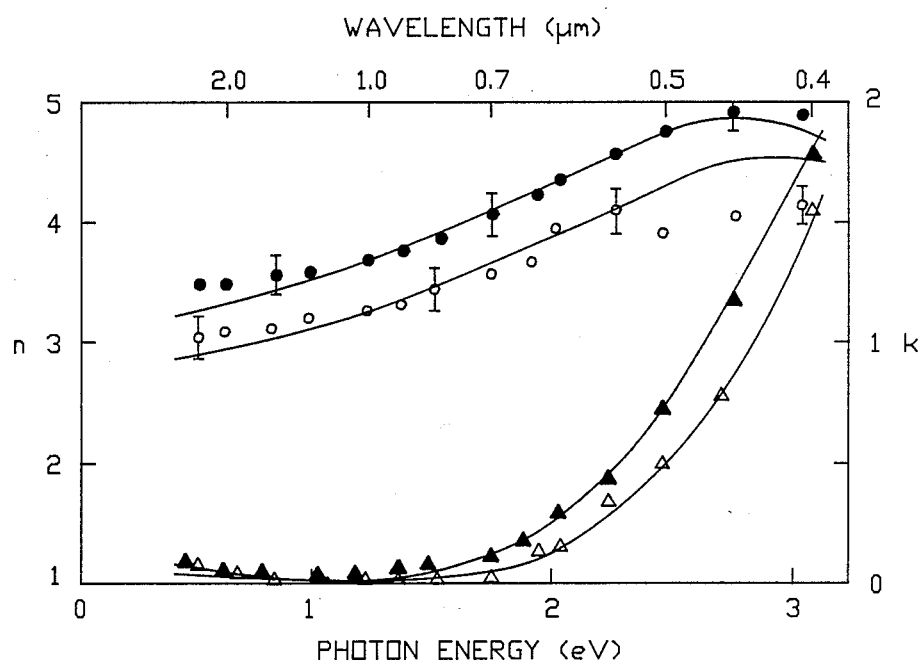
FIG. 4 shows the correspondence between the theoretical (solid lines) and the experimental data points. The experimental data points are from McKenzie et al for a-Si:H produced by sputtering of crystalline silicon in Ar/H$_2$ ambient (film number 3 of the original McKenzie et al reference) and k for a-Si:H with a different hydrogen content, also produced by sputtering of crystalline silicon in Ar/H$_2$ ambient (film number 4 of the original McKenzie et al reference).
Figure 5:
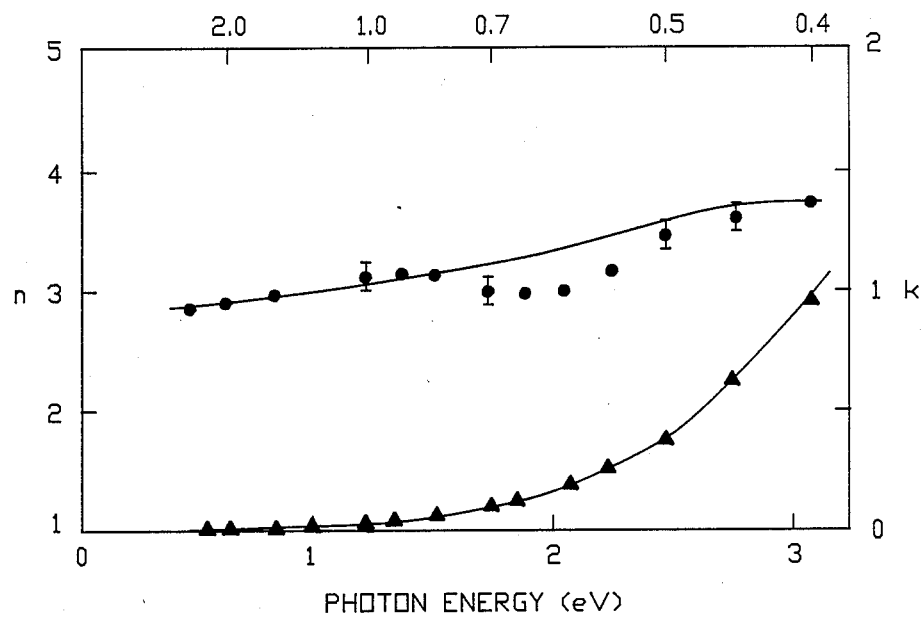
FIG. 5 shows the correspondence between the theoretical (solid lines) and the experimental data points. The experimental data points are from McKenzie et al for a-Si:H produced by glow-discharge composition of SiH$_4$ (film number 5 of the original McKenzie et al reference).

(ii) Experimental data presented in FIGS. 3–5 are from McKenzie et al, *J. Phys.* C16, 4933 (1982). The a-Si and a-Si:H films were deposited on heated (50° C.–200° C.) optical glass substrates, by DC magnetron reactive sputtering of crystalline silicon in an argon-hydrogen plasma, and by DC magnetron glow-discharge decomposition of silane in argon ambient. Values of n and k were determined by measuring spectral reflectance and transmittance of the film-substrate system at photon energies between 0.5 and 3.1 eV.

Evidence for the existence of an energy in the lower end of the spectrum at which k goes through a minimum is clearly seen in FIGS. 2–4. The corresponding energy of the minimum of k(E) is $E_g$ in our formulation.

Figure 6:
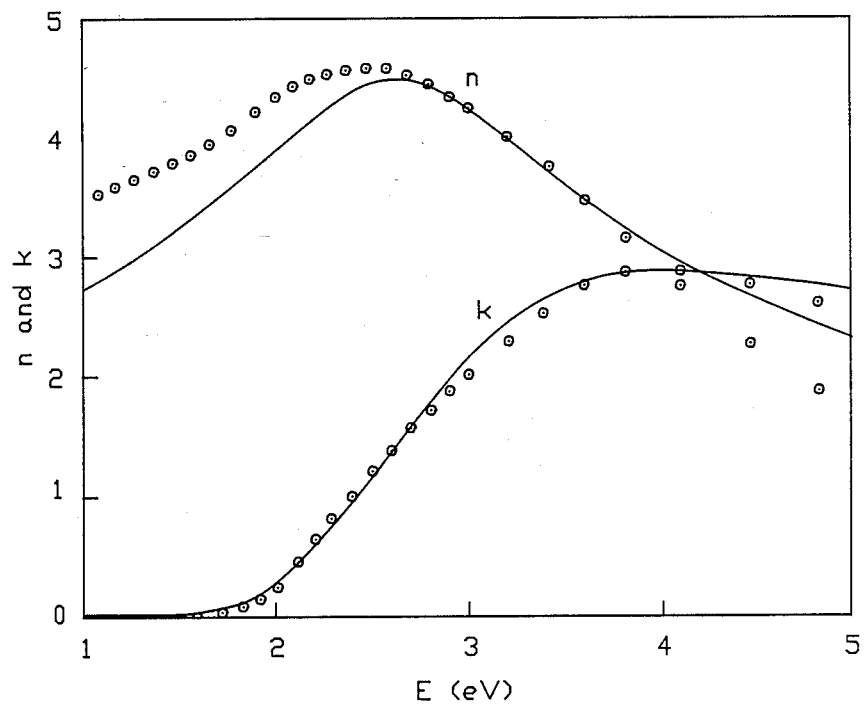
FIG. 6 shows the correspondence between the theoretical (solid lines) and the experimental data points from H. R. Philipp for a-Si produced by electron beam evaporation.

(iii) Experimental data presented in FIG. 6 are from H. R. Philipp, *J. Phys. Chem. solids* 32, 1935 (1971). The amorphous silicon thin film was formed on unheated glass substrate by electron beam evaporation of crystalline silicon. The optical constants were determined by Kramers-Kronig analysis of measured reflectance spectra. The poor correspondence between the experimental and theoretical n in FIG. 6, as well as FIG. 7, is probably due to errors introduced by extrapolation of reflectance data to the limits of integrations.

2. (a-Si$_3$N$_4$)

Dielectric thin films of amorphous silicon nitride (a-Si$_3$N$_4$) having different optical properties can also be produced if process conditions are varied. For example, it has been shown that a minute amount of excess silicon can transform an essentially transparent silicon nitride film into an opaque one in the near ultraviolet range.

Figure 7:
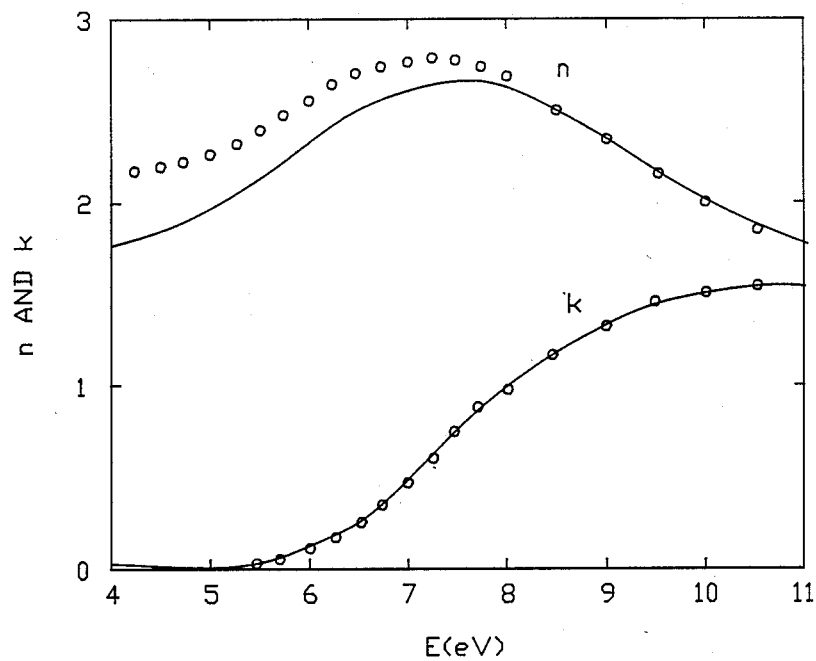
FIG. 7 shows the correspondence between the theoretical (solid lines) and the experimental data points are from Phillip for a-Si$_3$N$_4$ produced by pyrolytic decomposition of a mixture of silane and ammonia.

Experimental data presented in FIG. 7 are from H. R. Philipp in "*Handbook of Optical Constants of Solids*", edited by E. D. Palik (Academic Press, N.Y., 1985), p. 771. The noncrystalline silicon nitride film was deposited on bare single crystal silicon or quartz substrate by pyrolytic decomposition at 1000° C. of a mixture of SiH$_4$ and NH$_3$. (Silicon nitride prepared by high-temperature pyrolysis is generally considered to be stoichiometric Si$_3$N$_4$, containing a negligible amount of hydrogen.) The optical constants were determined by Kramers-Kronig analysis of reflectance and absorption data.

3. (a-TiO$_2$)

The optical constants of the semiconducting-dielectric non-crystalline titanium dioxide (a-TiO$_2$) thin films found in the literature show large differences, probably due to poorly defined composition (in spite of being referred to as TiO$_2$) caused by differences in preparation methods.

Figure 8:
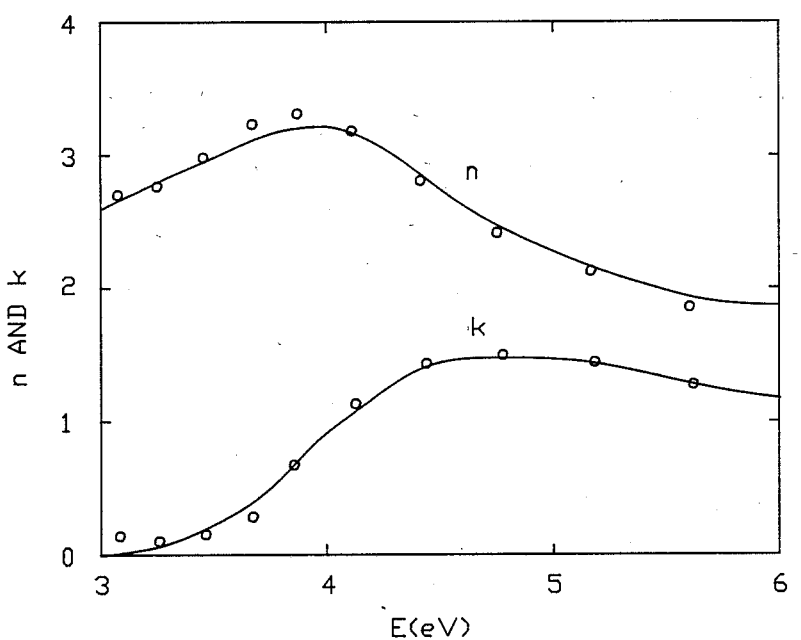
FIG. 8 shows the correspondence between the theoretical (solid lines) and the experimental data points are from J. Joseph and A. Gagnaire, Thin Solid Films 103, 257 (1983) for a-TiO$_2$ produced by anodic oxidation of titanium.

Experimental data presented in FIG. 8 are from J. Joseph et al, *Thin Solid Films* 103, 257 (1983). The film was produced by anodic oxidation of titanium sample. Although not explicitly discussed by Joseph et al, the film is most likely amorphous and not of rutile structure, the crystalline form of natural titanium dioxide. This is because rutile is optically anisotropic, whereas the titanium dioxide investigated appears to be isotropic. The optical constants were determined from analysis of ellipsometric measurements on a set of sample with different film thicknesses, in the wavelength rant 220–720 nm, corresponding to 5.6–1.8 eV.

Thus, we see that the measured optical constants, n and k, over a wide range of energies, for a variety of a-Si and a-Si:H, a-Si$_3$N$_4$, as well as for a-TiO$_2$, all appear to follow the simple analytical form given by equations (26) and (18).

II. Crystalline Semiconductors and Dielectrics

In crystalline semiconductors and dielectrics long range order gives rise to structure in k(E) containing several peaks, in contrast to a single peak in k(E) for the amorphous case. In order to account for these peaks, we first note that in the amorphous case the maximum for $\Phi(\omega)$, which occurs when . . .

When $\vec{k}=\vec{k}_{crit}$, then $\vec{\nabla}_k E_{cv}(\vec{k}_{crit})=0$. This condition is satisfied, for the most part, at symmetry points, or symmetry lines or planes in the Brillouin zone. Therefore, analogous to previous treatments, symmetry analysis of the Brillouin zone of these materials should determine which specific states are involved in transitions which produce peaks in k(E).

Thus, we take k(E) as a sum of terms, each term having the form given by Eq.(18), where the number of terms is equal to the number of peaks in k(E). The extinction coefficient for crystalline materials is then given by $$k(E) = \left( \sum_{i=1}^{q} \frac{A_i}{E^2 - B_i E + C_i} \right)(E - E_g)^2 \quad (q = \text{integer}) \quad \text{Eq.(37)}$$

where $$A_i = \text{const.} \; |<\psi_{crit}^c|x|\psi_{crit}^v>|^2 \gamma_i \quad \text{Eq.(38)}$$

$$B_i = 2\,[E_c(k_{crit}) - E_v(k_{crit})]_i \quad \text{Eq.(39)}$$

$$C_i = [E_c(k_{crit}) - E_v(k_{crit})]_i^2 + \frac{2\gamma_i^2}{4}. \quad \text{Eq.(40)}$$

In Eq.(38), $\Psi_{crit}^{c,v}$ denotes the electron state in the conduction or valence band when k=k$_{crit}$.

The refractive index, n(E), determined from Kramers-Kronig analysis as the Hilbert transform of Eq.(37), will then be given by:

$$n(E) = n(\infty) + \sum_{i=1}^{q} \frac{B_{0i}E + C_{0i}}{E^2 - B_i E + C_i} \quad (q = \text{integer}) \quad \text{Eq.(41)}$$

-continued where $$B_{0i} = \frac{A_i}{Q_i}\left(-\frac{B_i^2}{2} + E_g B_i - E_g^2 + C_i\right) \quad \text{Eq.(42)}$$

$$C_{0i} = \frac{A_i}{Q_i}\left[(E_g^2 + C_i)\frac{B_i}{2} - 2E_g C_i\right] \quad \text{Eq.(43)}$$

$$Q_i = \frac{1}{2}(4C_i - B_i^2)^{\frac{1}{2}} \quad \text{Eq.(44)}$$

In both the amorphous and crystalline case we do not assume that $n(\infty) = 1$, in contrast to classical dispersion theory. In fact, J. S. Toll [Ph.D. Thesis, Princeton University, N.J., 1952] has shown that mathematics dictates that $n(\infty) = 1 + cA$, where c represents the speed of light and the factor A represents a positive constant, when the condition of causality as well as the condition $k(E) \to 0$ as $E \to \infty$ are satisfied. Assuming these two conditions, and using the convention that $N(E) = n(E) + ik(E)$ (which gives N(E) analytic in the upper half plane), he derives the following dispersion relation:

$$N(\omega_r) = 1 + cA + (c/\pi)\lim_{\omega_i \to 0+} \quad \text{Eq.(45)}$$

$$\int_0^\infty \alpha(\omega_r')d\omega_r'/\omega_r'^2 - (\omega_r + i\omega_i)^2$$

where $\omega_r$ and $\omega_i$ are the real and imaginary parts of the complex frequency $\omega = \omega_r + i\omega_i$ and $\alpha$ is the absorption coefficient.

Substituting for k(E) in Eq.(45) gives:

$$N(\omega_r) = 1 + cA + (1/\pi)\lim_{\omega_i \to 0+} \quad \text{Eq.(46)}$$

$$\int_{-\infty}^\infty k(\omega_r')d\omega_r'/\omega_r' - \omega_r + i\omega_i,$$

which is equivalent to $$n(E) = 1 + cA + (1/\pi)P\int_{-\infty}^\infty k(E') - dE'/E' - E. \quad \text{Eq.(47)}$$

Toll interprets the term cA in Eq.(47) as arising from an absorption line at infinity. This term may seem physically implausible, since the condition that $k(E) \to 0$ as $E \to \infty$ is incorporated; however, as Toll points out, the term is "logically permitted by the Principle of Limiting Distances... Mathematical deduction does not exclude this term. It has to be explicitly excluded on other grounds."

Toll's derivation for $n(\infty) = 1 + cA$ can trivially be extended to the case at hand where the Principle of Limiting Distance is satisfied by $k(E) \to$ constant as $E \to \infty$. A subtraction of $k(\infty)$ in the integral of Eq.(47) is all that is needed so that $$n(E) = 1 + cA + \quad \text{Eq.(48)}$$

$$(1/\pi)\int_{-\infty}^\infty [k(E') - k(\infty)]dE'/E' - E.$$

giving $n(\infty) = 1 + cA > 1$ in this more general case. Given that $k(\infty) \neq 0$, it would seem illogical to exclude the term cA on physical grounds, since $n(\infty) = 1$ implies no interaction for $E \to \infty$. Thus, $n(\infty)$ is greater than one because there is absorption in the limit $E \to \infty$.

Examples For Crystalline Materials

In this section we will apply Eqs.(37) and (41) to published experimental data. It will be shown that these equations describe, over a wide range of photon energies, the optical constants of a large number of crystalline semiconductor and dielectric materials. We will also show that the real, $\epsilon_1(E) = n^2(E) - k^2(E)$, and imaginary, $\epsilon_2(E) = 2n(E)k(E)$, parts of the complex dielectric function, $\epsilon(E) = \epsilon_1(E) - i\epsilon_2(E)$, as well as normal-incidence reflectance spectrum, $$R(E) = [n(E) - 1]^2 + k(E)/[n(E) + 1]^2 + k^2(E),$$

can be described when n(E) and k(E) are given by Eqs.(37) and (41).

a. The Data

Measured values of the optical constants of many materials, reported by different investigators, are compiled in "*Handbook of Optical Constants of Solids*", edited by E. D. Palik (Academic, N.Y., 1985). However, as pointed out by Aspnes and Studna [Phys. Rev. B27, 985 (1983)], discrepancies of the order of 10-30% are common in "seemingly equally valid" data.

For the present patent application, we selected crystalline solids for which n and k were available in tabulated form, for a relatively wide range of energies, measured in the same laboratory. This provided a measure of consistency. The selected crystalline solids are group IV semiconductors (Si and Ge), group III-V semiconductors (GaP, GaAS, GaSb, InP, InAs, and InSb), group IV-IV semiconductor (SiC), and crystalline insulators (cubic-C and $\alpha$-SiO$_2$).

The optical constants for Si, Ge, GaP, GaAs, GaSb, InP, InAs, and InSb, in the 1.5 to 6.0 eV range, are by Aspnes and Studna [Phys. Rev. B27, 985 (1983)]. Beyond this range (and sometimes overlapping at end points) data for some of these materials from other sources (see, e.g., *Handbook of Optical Constants of Solids*) were also included. This was done mainly to include large peaks in k spectrum and also to elucidate discrepancies.

Experimental data for SiC ($\sim$5 to 13 eV), cubic-C ($\sim$5 to 18 eV), and $\alpha$-SiO$_2$ ($\sim$2 to 18 eV) are by G. Leveque and D. A. Lynch, privately communicated to W. J. Choyke and E. D. Palik. See H. R. Philipp and E. A. Taft, Phys. Rev. 136, A1445 (1964), quoted in tabulated form by D. F. Edwards and H. R. Philipp and H. R. Philipp, solid State Commun. 4, 73 (1966).

b. The Band Gap, $E_g$

The values of $E_g$ for various materials quoted in the literature are obtained, usually, by extrapolating the "linear" portion of the plot of $(\alpha \hbar\omega)^{1/m}$ versus $\hbar x$, where $m = \frac{1}{2}$, 3/2, or 2, depending on the assumed mode of optical transition (allowed direct, forbidden, or indirect, respectively). The quoted value of $E_g$ (say, at room temperature) for a given semiconductor may thus vary depending on the method of extrapolation and mode of transition.

TABLE 1

FILM CHARACTERIZATION

| Film ID# in the original reference | Film | Preparation method (ambient) | at. % H | $E_{min} = E_g$ in eV | $E_{max}$ in eV | $k_{max}$ | $k_{fit}$ ($E_{fit}$ in eV) | $n_{fit}$ ($E_{fit}$ in eV) |
|---|---|---|---|---|---|---|---|---|
| 2 | a-Si* | sputtering (Ar/H$_2$) | not given | 1.3 | 4.33 | 2.2 | 0.52 (2.3) | 4 (1.959) |
| 3 | a-Si* | glow discharge | not given | 1.65 | 4.55 | 2.55 | 0.55 (2.5) | 4.05 (1.959) |
| 1 | a-Si | sputtering (Ar) | 0 | 0.95 | 3.45 | 2.5 | 0.5 (1.95) | 5 (1.959) |
| 3 | a-Si:H | sputtering (Ar/H$_2$) | 8–10 | 1.15 | 3.95 | 2.5 | 0.5 (2.3) | 4.3 (1.959) |
| 4 | a-Si:H | sputtering (Ar/H$_2$) | 20–30 | 1.35 | 4.15 | 2.5 | 0.5 (2.5) | 3.8 (1.959) |
| 5 | a-Si:H | glow discharge | 20–30 | 0.475 | 3.975 | 1.7 | 0.3 (2.375) | 3.3 (1.959) |
| — | a-Si | E-beam evaporation | 0 | 1.3 | 4 | 2.89 | 1.384 (2.6) | 4.213 (3) |
| — | a-Si$_3$N$_4$ | pyrolytic | negligible | 4.75 | 10.5 | 1.53 | 0.866 (7.75) | 2.492 (8.5) |
| — | a-TiO$_2$** | anodic oxidation of titanium | not applicable | 2.8 | 4.768 | 1.485 | 0.65 (3.875) | 3.148 (4.133) |

EVALUATED CONSTANTS

| A | B | C | $B_0$ | $C_0$ | n(∞) | THE ORIGINAL REFERENCES |
|---|---|---|---|---|---|---|
| 1.2231 | 5.2631 | 9.1867 | 0.4005 | 3.8846 | 2.2792 | Klazes et al. |
| 1.5690 | 5.5311 | 9.9630 | 0.8298 | 2.6444 | 2.4330 | |
| 0.9000 | 5.1000 | 7.9425 | −0.8400 | 5.5980 | 2.7908 | McKenzie et al. |
| 0.8494 | 5.9972 | 10.7504 | −1.0623 | 7.3507 | 2.4440 | |
| 0.8494 | 6.3972 | 11.9898 | −1.0623 | 7.5631 | 2.1362 | |
| 0.2242 | 7.0266 | 13.7460 | −1.4822 | 6.8215 | 2.2739 | |
| 1.4910 | 5.2139 | 8.6170 | 0.1242 | 4.9351 | 1.5256 | H. R. Philipp |
| 0.8000 | 14.9868 | 64.4000 | 0.2010 | 11.1000 | 1.1089 | H. R. Philipp |
| 0.5189 | 8.1605 | 17.5291 | −0.4195 | 2.9587 | 1.7614 | J. Joseph et al. |

*Expect the films to be a-Si:H due to their preparation methods.
**Non-crystalline titanium oxide, probably with poorly defined stoichiometry.

In our formulation, $E_g$ specifies the position of absolute minimum in k spectrum. Experimentally, the absolute minimum occurs at the onset of the "fundamental" absorption edge (e.g., see k spectra for various crystalline semiconductors and dielectrics in *The Handbook of Optical Constants of Solids*). Thus, we have taken $E_g$ (listed in Tables 2, 3, and 4) as such.

Figure 9:
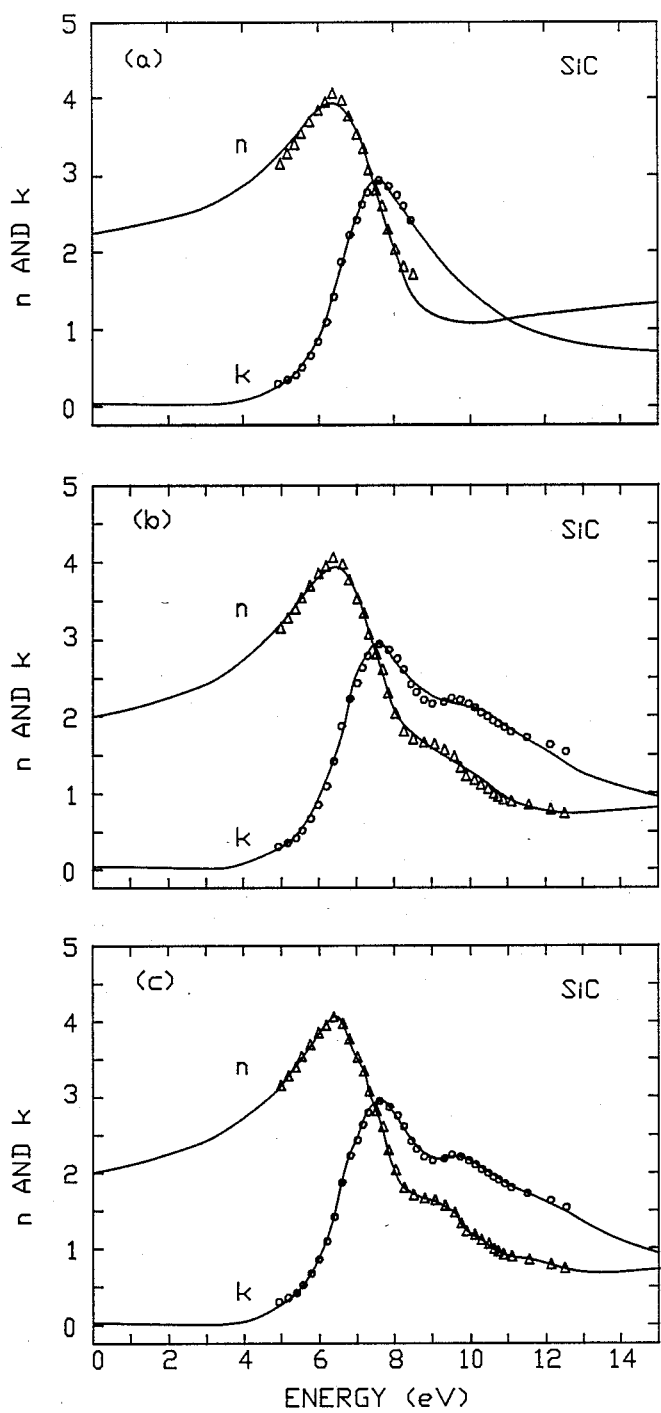
FIG. 9 shows the solid lines that are the theoretical plots of n(E) and k(E) given by Eqs.(41) and (37) with the parameters specified in Table 1 for crystalline SiC, taking the number of terms equal to 1, 2, and 4 in (a), (b) and (c), respectively. In (a) only experimental data in the 5 to 8.5 eV range are considered and the experimental data are by G. Leveque and D. A. Lynch.
Figure 10A:
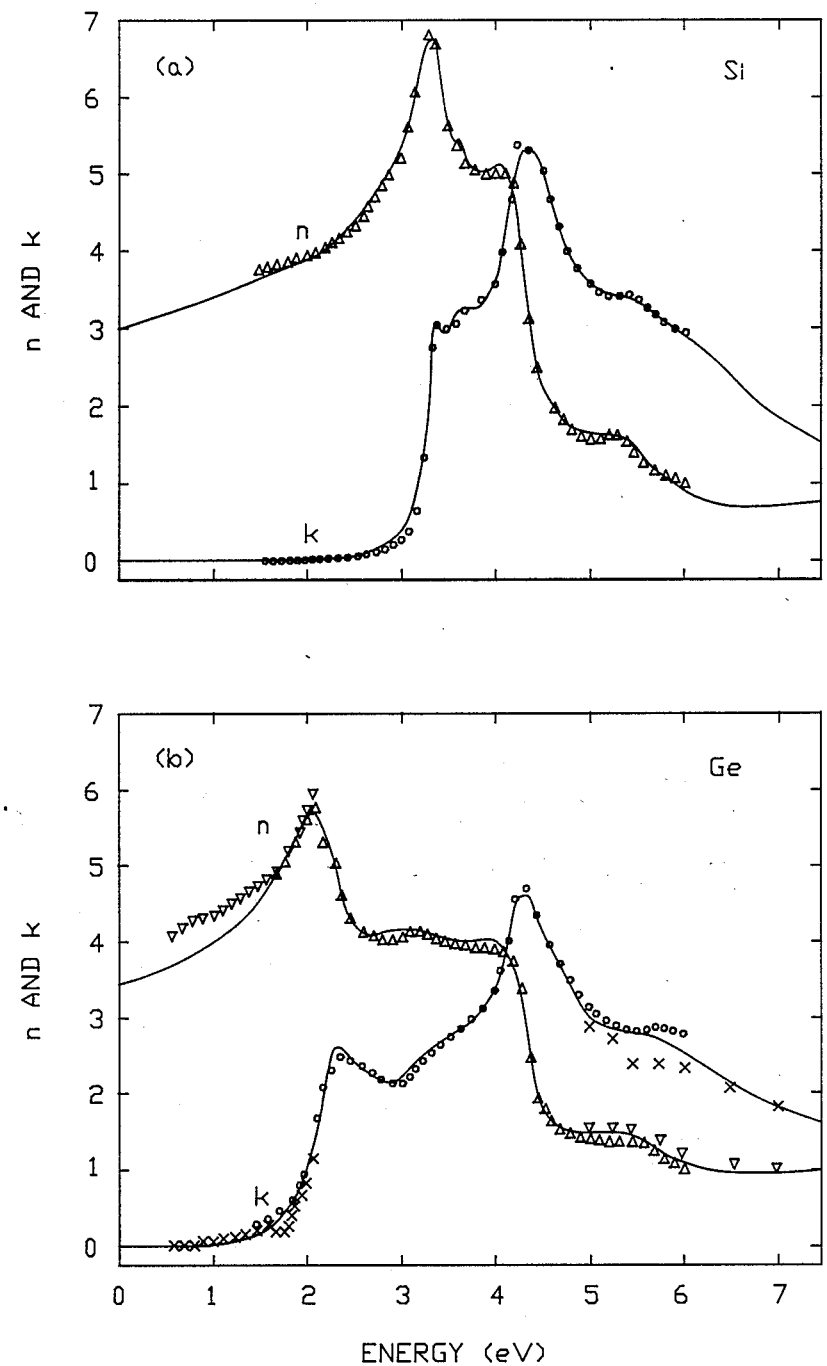
FIG. 10 shows the solid lines that are the theoretical plots of n(E) and k(E) given by Eqs.(41) and (37) with the parameters specified in Table 2 for crystalline Si, Ge, GaP, GaAs, GaSb, InP, InAs, and InSb, where n:Δ and k:• are experimental data points from D. E. Aspnes and A. A. Studna, Phys. Rev. B 27, 985 (1983), and where n: ∇ and k:x are experimental data points by Leveque and Lynch.
Figure 10B:
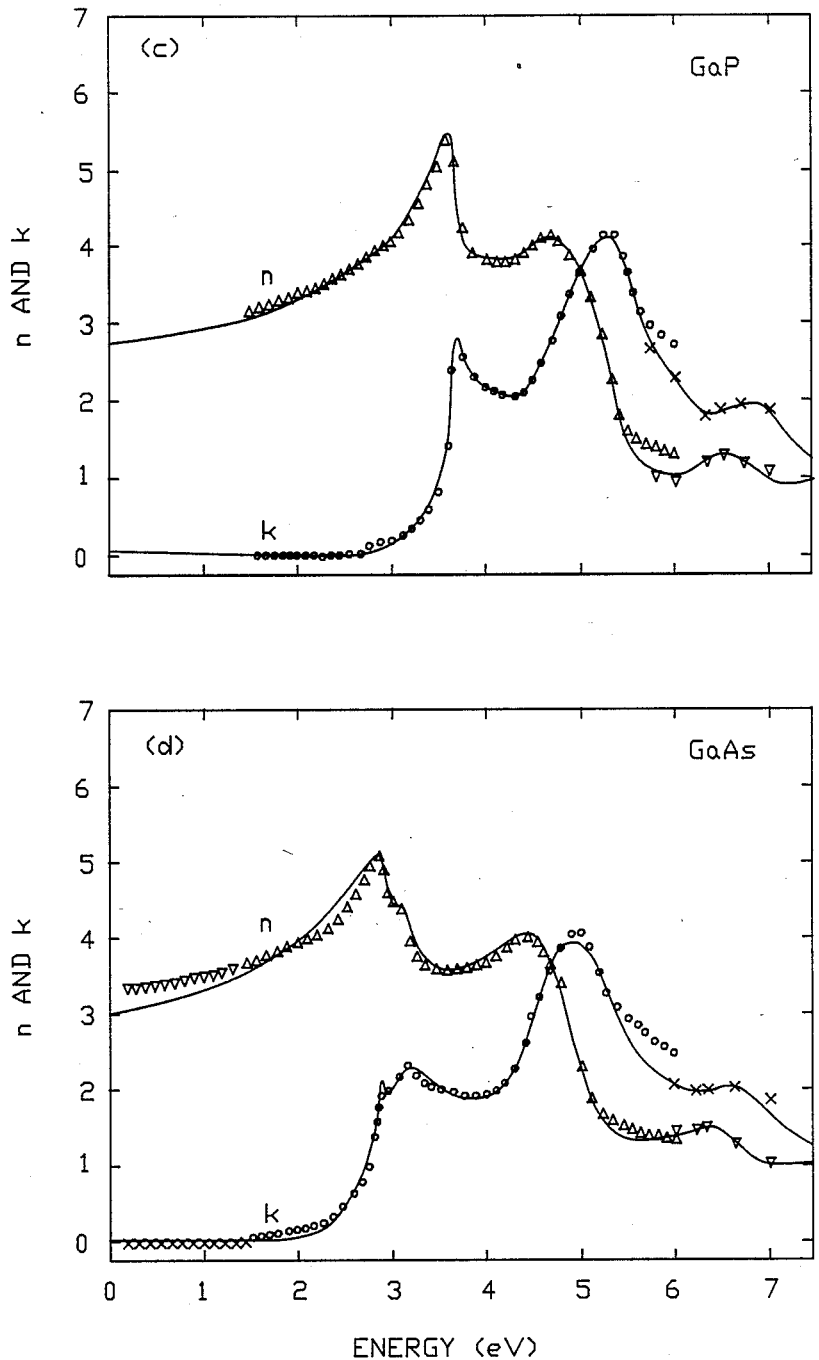
Figure 10C:
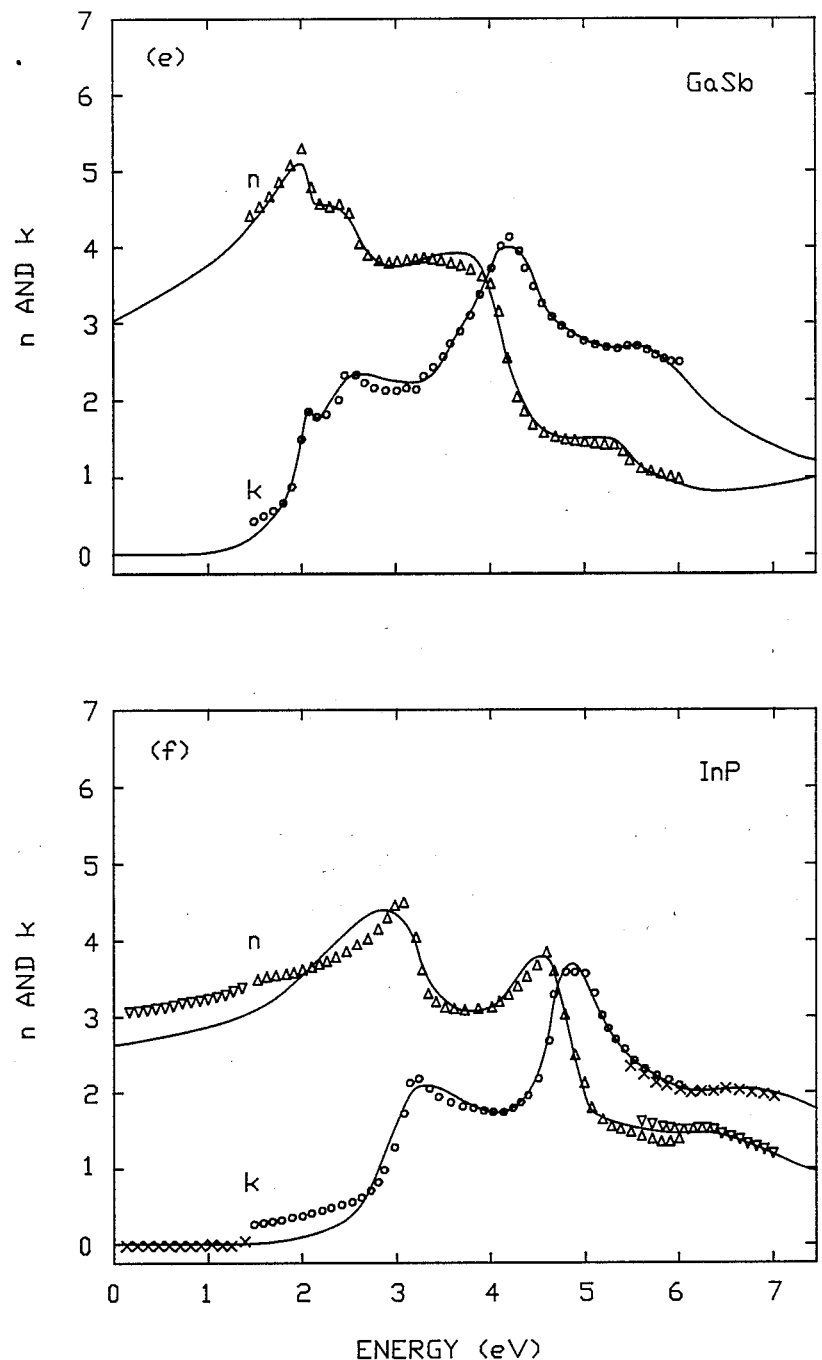
Figure 10D:
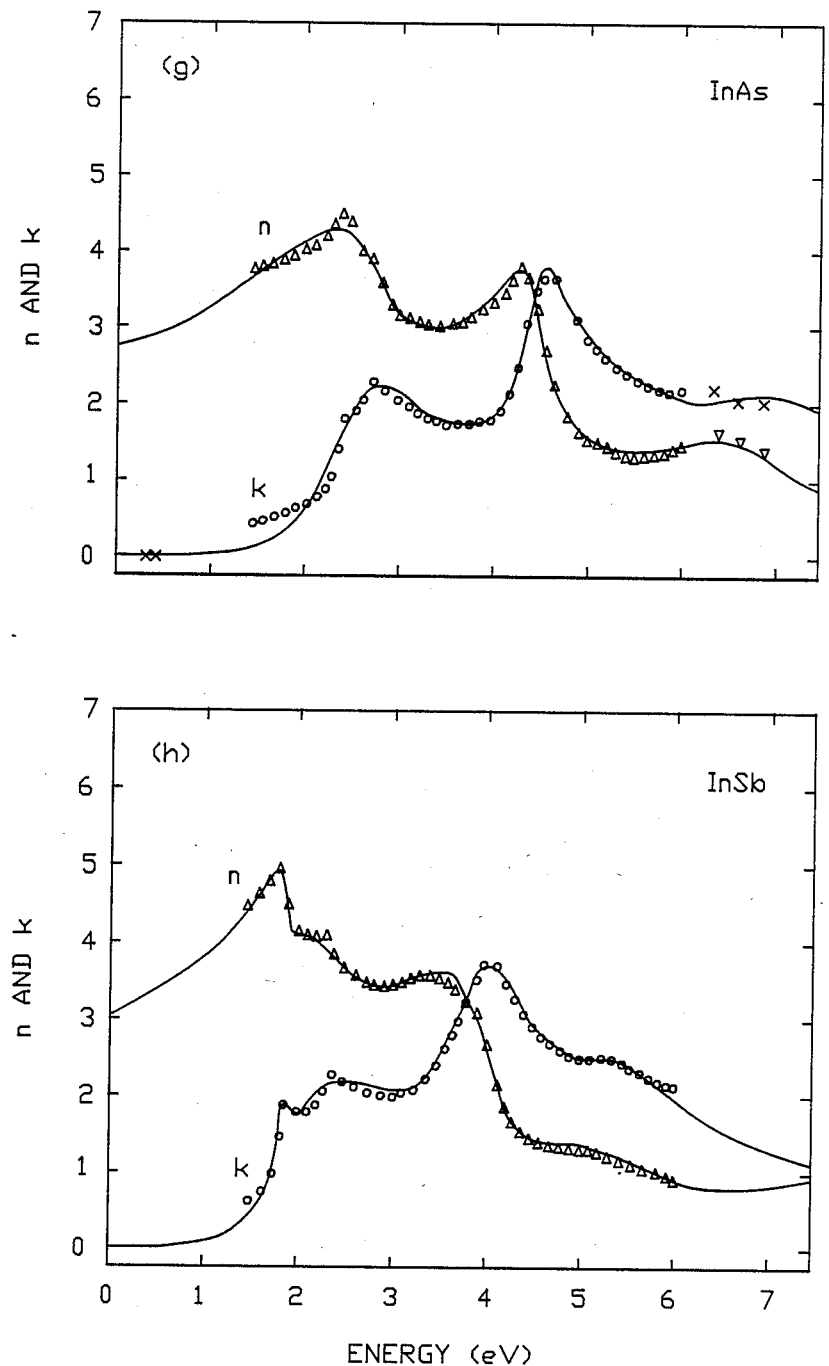

In Table 2, values of the parameters $A_i$, $B_i$, $C_i$, and n(∞) for crystalline SiC, obtained by least-square fitting of experimental n and k data to Eqs.(41) and (37), taking the number of terms equal to either 1, 2, or 4. The energy band gap of SiC is also given. The corresponding theoretical plots of n(E) and k(E) are shown in FIG. 9.

TABLE 2

| | $A_i$ | $B_i$ | $C_i$ | n(∞) | $E_g$ |
|---|---|---|---|---|---|
| 1 term | 0.25926 | 14.359 | 53.747 | 1.680 | 0 |
| 2 terms | 0.18028 | 14.222 | 52.148 | 1.337 | |
| | 0.10700 | 19.397 | 99.605 | | |
| 4 terms | 0.00108 | 13.227 | 43.798 | 1.353 | |
| | 0.19054 | 14.447 | 53.860 | | |
| | 0.00646 | 19.335 | 94.105 | | |
| | 0.05366 | 21.940 | 125.443 | | |

Figure 11:
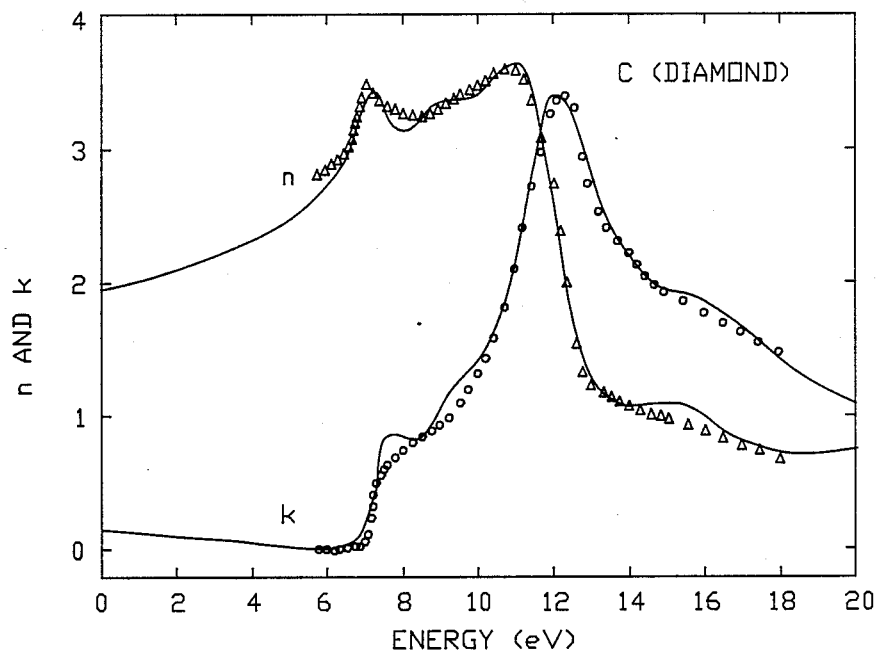
FIG. 11 shows the solid lines that are the theoretical plots of n(E) and k(E) given by Eqs.(41) and (37) with the parameters specified in Table 2 for crystalline cubic-C, where n:Δ and k:• are experimental data points by H. R. Philipp and E. A. Taft, Phys. Rev. 136, A1445 (1964).
Figure 12:
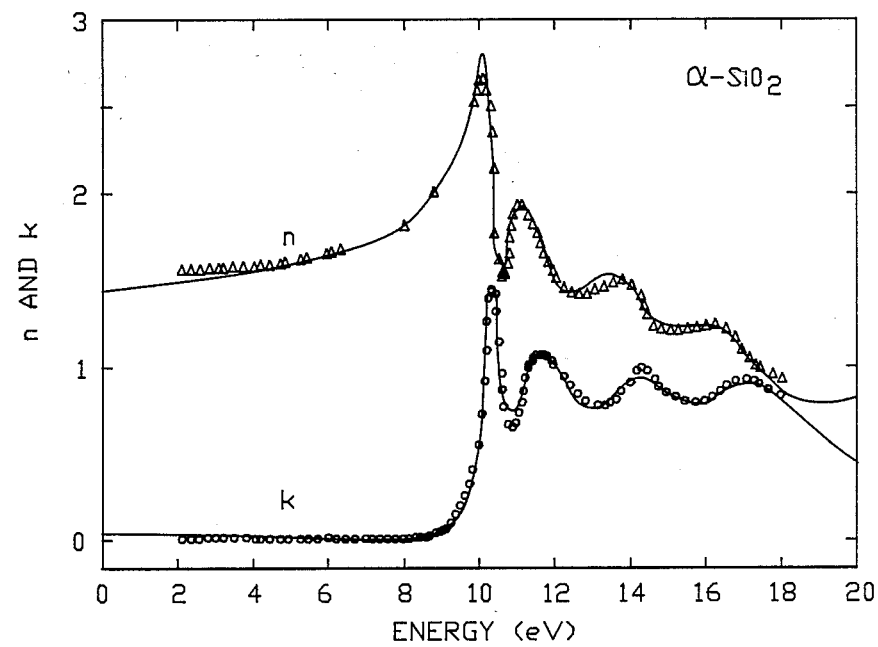
FIG. 12 shows the solid lines that are the theoretical plots of n(E) and k(E) given by Eqs.(41) and (37) with the parameters specified in Table 2 for crystalline α-SiO$_2$, where n:ϕ and k:• are experimental data points by H. R. Philipp, Solid State Commun. 4, 73 (1966).
Figure 13:
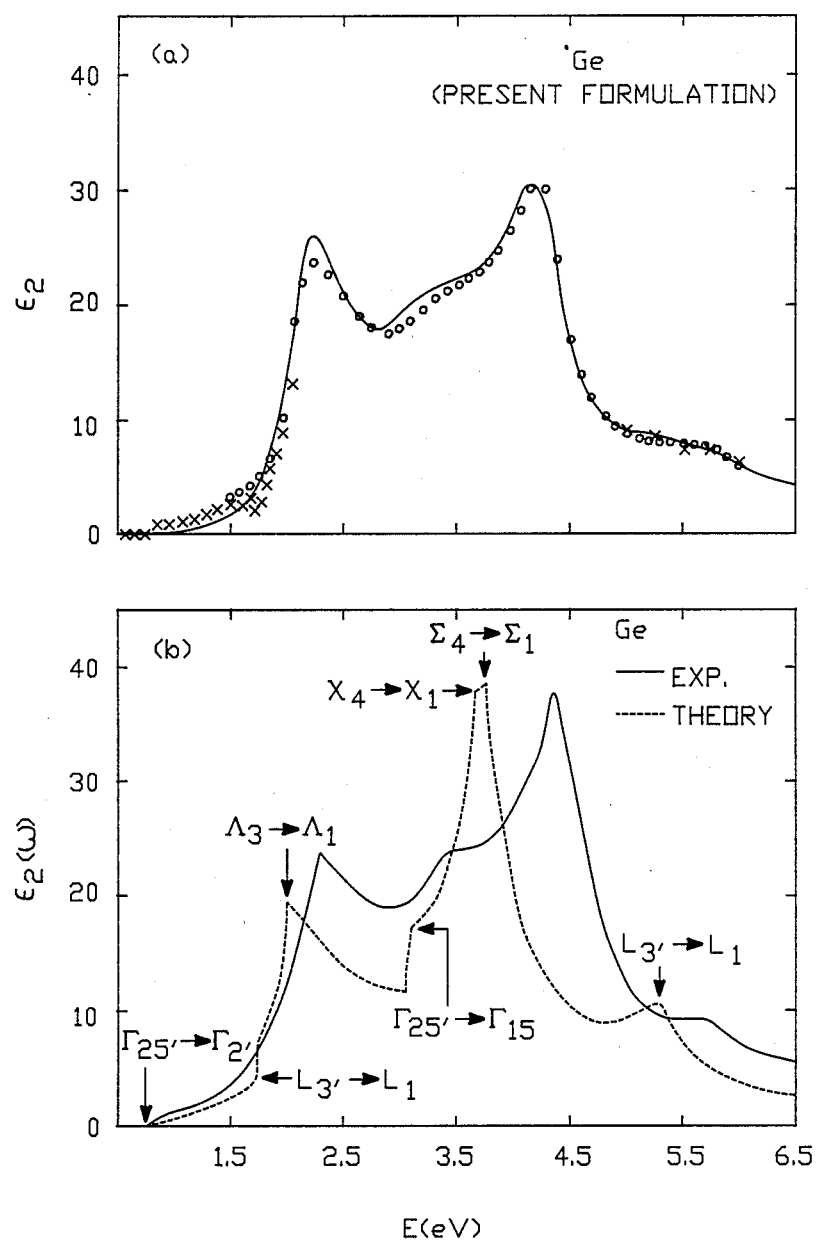
FIG. 13 shows (a) the solid line that is the theoretical plot of $\epsilon_2(E)=2n(E)k(E)$, where n(E) and k(E) are given by Eqs.(41) and (37) with the parameters specified in Table 2 for crystalline Ge. The experimental $\epsilon_2$ data points • and x are from Aspnes and Studna and *Handbook of Optical Constants of Solids*, edited by E. D. Palik (Academic, N.Y., 1985), respectively; and (b) Pseudopotential calculation of $\epsilon_2$ for Ge by D. Brust, J. C. Phillips, and F. Bassani, Phys. Rev. Lett. 9, 94 (1962), and D. Brust, Phys. Rev. 134, A1337 (1964). A typical assignment of critical point transitions to the major peaks and edges is shown. The 4.5 eV peak is attributed to the accidental degeneracy of an M$_1$ edge due to X$_4$→X$_1$ transition and an M$_2$ edge due to $\Sigma_4$→$\Sigma_1$ transition. The 2.1 eV edge is attributed to an M$_1$ critical point due to $\Lambda_3$→$\Lambda_1$ transition. Exciton-like effects (electron-hole interactions), causing line narrowing, are attributed to these transitions. The edge at 0.8 eV (argued to be a direct threshold) is attributed to an M$_0$ edge due to $\Gamma_{25}$, →$\Gamma_2$, transition. Notation for the edges M$_0$, M$_1$, M$_2$ is detailed in D. L. Greenaway and G. Harbeke, *Optical Properties and Band Structure of Semiconductors* (Pergamon, Oxford, 1968) and C. Phillips, *Bonds and Bands in Semiconductors* (Academic, N.Y., 1973), while notation for the states of X, Σ, Γ, is detailed in D. L. Greenaway and G. Harbeke, *Optical Properties and Band Structure of Semiconductors* (Pergamon, Oxford, 1968) and A. Nussbaum, in *Solid State Physics*, edited by F. Seitz and D. Turnbull (Academic, N.Y., 1966), Vol. 18, p. 165.
Figure 14:
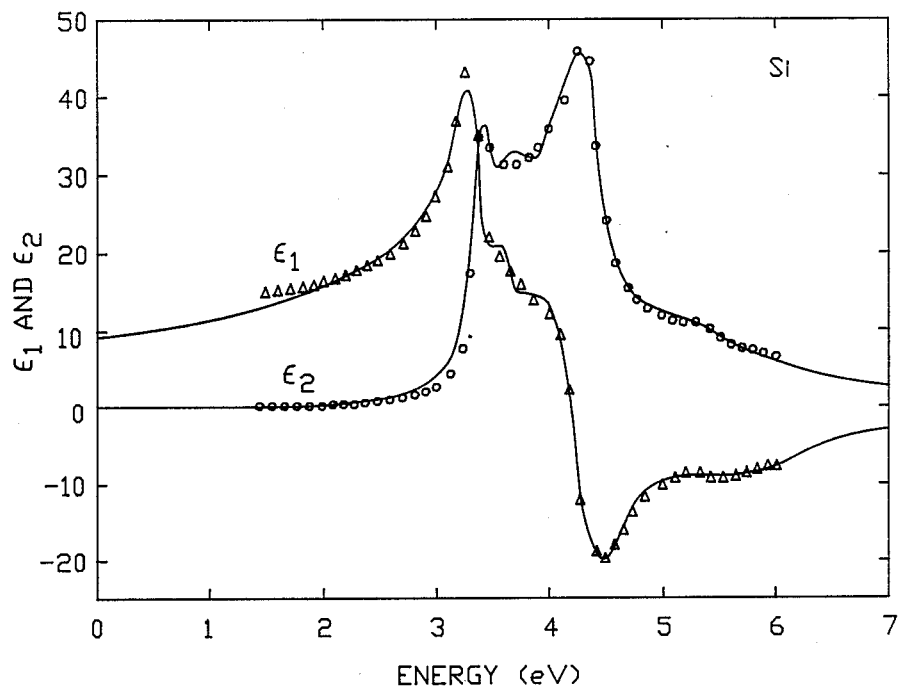
FIG. 14 shows the solid lines that are the theoretical plots of $\epsilon_1(E)=n^2(E)-k^2(E)$ and $\epsilon_2(E)=2n(E)k(E)$, where n(E) and k(E) are given by Eqs.(41) and (37) with the parameters specified in Table 2 for crystalline Si. $\epsilon_1$:Δ and $\epsilon_2$:• experimental data are from Aspnes and Studna.

In Table 3, values of the parameters $A_i$, $B_i$, $C_i$, and n(∞) for different crystalline materials, obtained by least-square fitting of experimental n and k data to Eqs.(47) and (37), taking the number of terms equal to 4. The energy band gaps of these materials are also given. The corresponding theoretical plots of n(E) and k(E) are shown in FIGS. 10–12. The theoretical plots of $\epsilon_2(E)$ for Ge, and $\epsilon_1(E)$ and $\epsilon_2(E)$ for Si, are shown in FIG. 13(a) and FIG. 14.

TABLE 3

| | $A_i$ | $B_i$ | $C_i$ | n(∞) | $E_g$ |
|---|---|---|---|---|---|
| Si | 0.00405 | 6.885 | 11.864 | 1.950 | 1.06 |
| | 0.01427 | 7.401 | 13.754 | | |
| | 0.06830 | 8.634 | 18.812 | | |
| | 0.17488 | 10.652 | 29.841 | | |
| Ge | 0.08556 | 4.589 | 5.382 | 2.046 | 0.60 |
| | 0.21882 | 6.505 | 11.486 | | |
| | 0.02563 | 8.712 | 19.126 | | |
| | 0.07754 | 10.982 | 31.620 | | |
| GaP | 0.00652 | 7.469 | 13.958 | 2.070 | 2.17 |
| | 0.14427 | 7.684 | 15.041 | | |
| | 0.13969 | 10.237 | 26.567 | | |
| | 0.00548 | 13.775 | 47.612 | | |
| GaAs | 0.00041 | 5.871 | 8.619 | 2.156 | 1.35 |
| | 0.20049 | 6.154 | 9.784 | | |
| | 0.09688 | 9.679 | 23.803 | | |
| | 0.01008 | 13.232 | 44.119 | | |
| GaSb | 0.00268 | 4.127 | 4.267 | 1.914 | 0.65 |
| | 0.34046 | 4.664 | 5.983 | | |
| | 0.8611 | 8.162 | 17.031 | | |
| | 0.02692 | 11.146 | 31.691 | | |
| InP | 0.20242 | 6.311 | 10.357 | 1.766 | 1.27 |
| | 0.02339 | 9.662 | 23.472 | | |
| | 0.03073 | 10.726 | 29.360 | | |
| | 0.04404 | 13.604 | 47.602 | | |
| InAs | 0.18463 | 5.277 | 7.504 | 1.691 | 0.30 |
| | 0.00941 | 9.130 | 20.934 | | |
| | 0.05242 | 9.865 | 25.172 | | |
| | 0.03467 | 13.956 | 50.062 | | |
| InSb | 0.00296 | 3.741 | 3.510 | 1.803 | 0.12 |
| | 0.22174 | 4.429 | 5.447 | | |
| | 0.06076 | 7.881 | 15.887 | | |
| | 0.04537 | 10.765 | 30.119 | | |
| Cubic-C | 0.10525 | 15.027 | 56.859 | 1.419 | 6.00 |
| | 0.08604 | 18.506 | 87.212 | | |
| | 0.14945 | 23.736 | 142.794 | | |
| | 0.04472 | 31.468 | 253.515 | | |
| α-SiO$_2$ | 0.00867 | 20.729 | 107.499 | 1.226 | 7.00 |
| | 0.02948 | 23.273 | 136.132 | | |
| | 0.01908 | 28.163 | 199.876 | | |

TABLE 3-continued

| | $A_i$ | $B_i$ | $C_i$ | $n(\infty)$ | $E_g$ |
|---|---|---|---|---|---|
| | 0.01711 | 34.301 | 297.062 | | |

Figure 15:
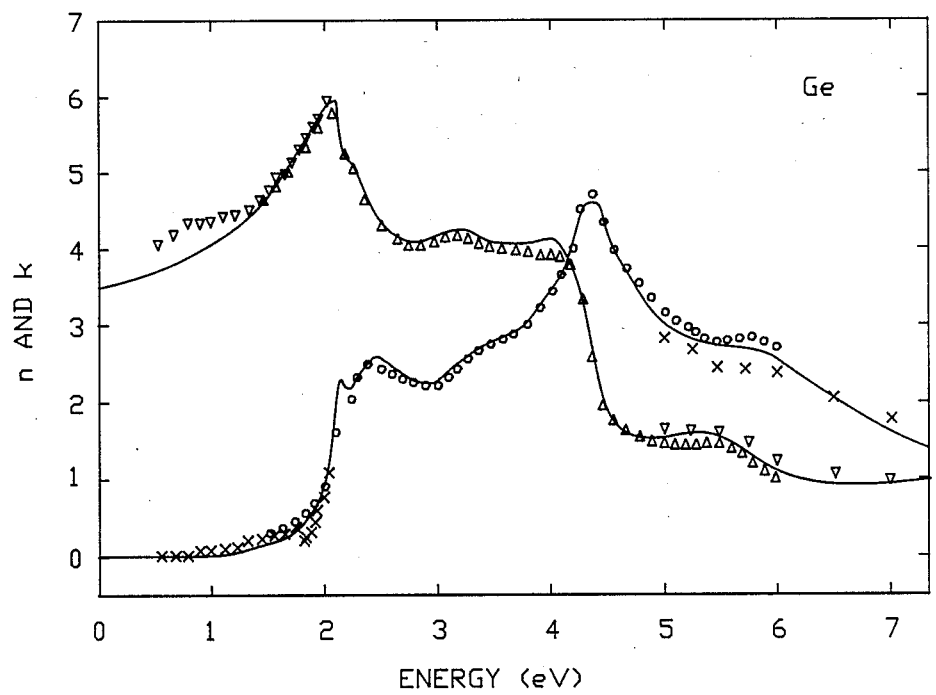
FIG. 15 shows the solid lines that are the theoretical plots of n(E) and k(E) given by Eqs.(41) and (37) with the parameters specified in Table III for crystalline Ge. n:Δ and k:• experimental data are from Aspnes and Studna. n: ∇ and k:x experimental data are from *Handbook of Optical Constants of Solids*.
Figure 16:
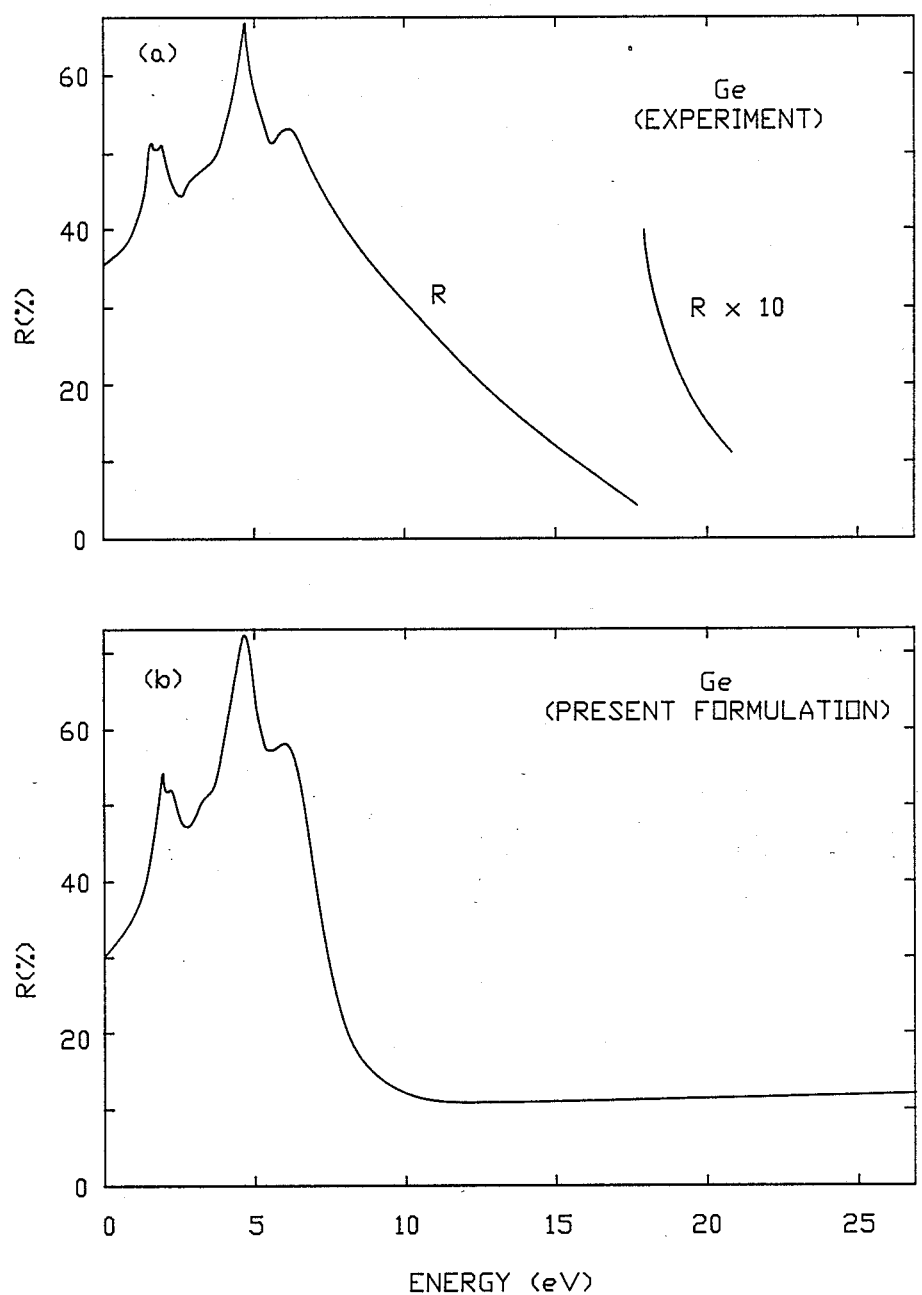
FIG. 16 shows (a) experimental reflectance spectrum of crystalline Ge taken from H. R. Philipp and H. Ehrenreich, Phys. Rev. 129, 1550 (1963); and (b) theoretical reflectance spectrum, $R(E)=\nabla\{[n(E)-1]^2+k^2(E)\}/\{[n(E)+1]^2+k^2(E)\}$, where n(E) and k(E) are given by Eqs.(41) and (37) with the parameters specified in Table 3 for crystalline Ge.

In Table 4, values of the parameters $A_i$, $B_i$, $C_i$, and $n(\infty)$ for crystalline Ge, obtained by least-square fitting of experimental n and k data to Eqs. (41) and (37), taking the number of terms equal to 5. The energy band gap of Ge is also given. The corresponding theoretical plots of n(E), k(E), and R(E) are shown in FIGS. 15 and 16.

TABLE 4

| | $A_i$ | $B_i$ | $C_i$ | $n(\infty)$ | $E_g$ |
|---|---|---|---|---|---|
| Ge | 0.00103 | 4.313 | 4.654 | 2.161 | 0.60 |
| (5 | 0.11637 | 4.677 | 5.639 | | |
| terms) | 0.10968 | 6.728 | 11.858 | | |
| | 0.03479 | 8.704 | 19.119 | | |
| | 0.07711 | 11.056 | 31.879 | | |

Figure 17:
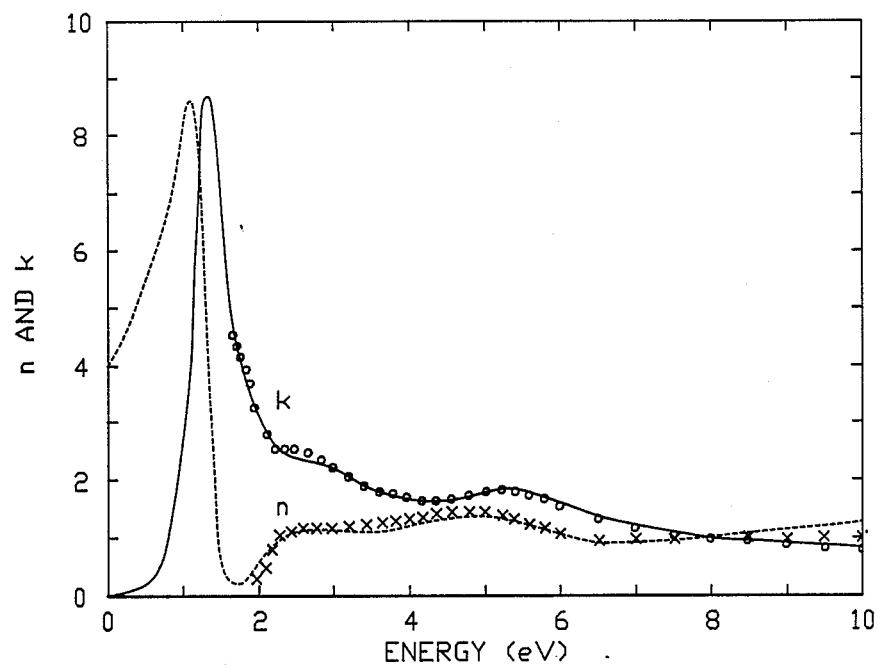
FIG. 17 shows the dashed and solid lines that are the theoretical plots of n(E) and k(E), respectively, given by Eqs.(50) and (49), with the parameters specified in Table V for copper. Experimental data (n:x and k:•) are taken from *Handbook of Optical Constants of Solids*.

In Table 5, values of the parameters $A_i$, $B_i$, $C_i$, and $n(\infty)$ for copper obtained by least-square fitting of experimental n and k data to Eqs. (50) and (49), taking the number of terms equal to 3. The corresponding theoretical plots of n(E) and k(E) are shown if FIG. 17.

TABLE 5

| | $A_i$ | $B_i$ | $C_i$ | $n(\infty)$ |
|---|---|---|---|---|
| Copper | 0.0094946 | 2.499 | 1.651 | 1.711 |
| | 0.07494 | 5.389 | 8.007 | |
| | 0.03872 | 10.394 | 28.386 | |

Figure 18:
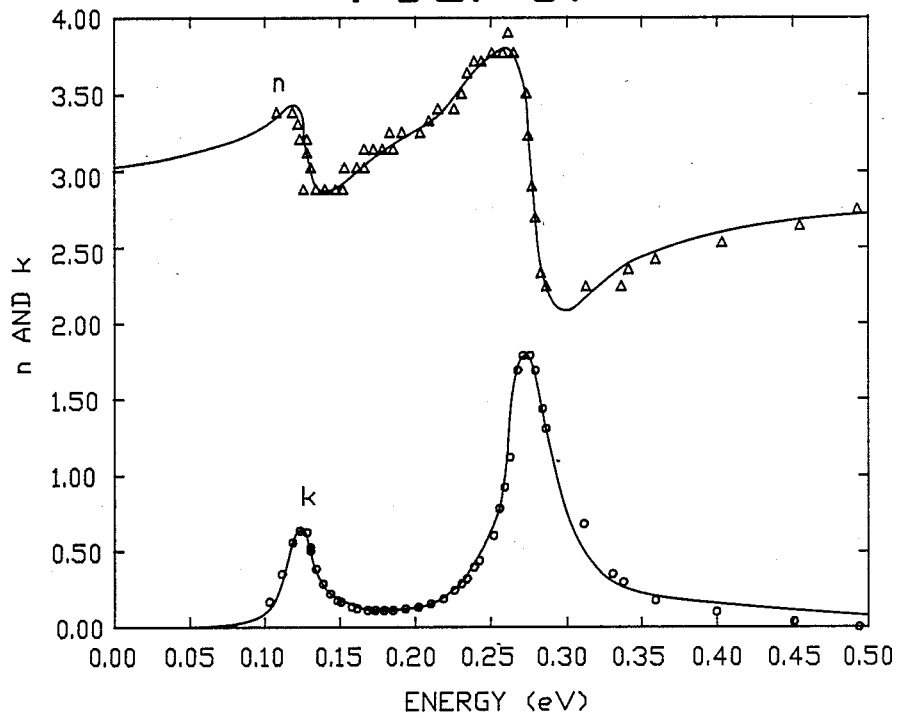
FIG. 18 shows the solid lines that are the theoretical plots of n(E) and k(E) given by Eqs.(41) and (37), with the parameters specified in Table 6 for vitreous As$_2$Se$_3$. Experimental data (n:Δ and k:•) are taken from *Handbook of Optical Constants of Solids*.
Figure 19:
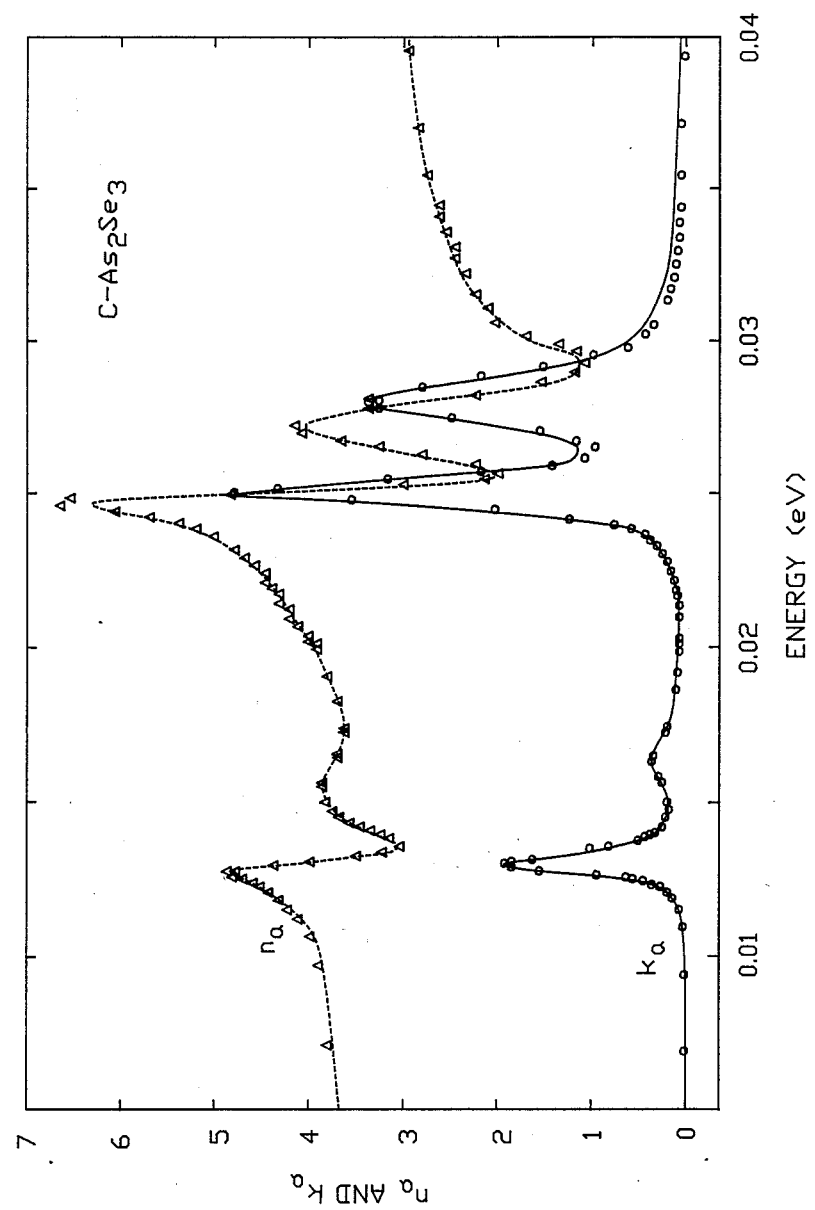
FIG. 19 shows the dashed and solid lines that are the theoretical plots of n(E) and k(E), respectively, given by Eqs.(41) and (37), with the parameters specified in Table VI for the crystalline $As_2Se_3$. Experimental data (n:Δ and k:●) are taken from *Handbook of Optical Constants of Solids*.

In Table 6, values of the parameters $A_i$, $B_i$, $C_i$, and $n(\infty)$ for vitreous and crystalline $As_2Se_3$ obtained by least-square fitting of experimental n and k to Eqs. (41) and (37), with $E_g=0$, and number of terms equal to 2 and 4, respectively. The corresponding theoretical plots of n(E) and k(E) are shown in FIGS. 18 and 19.

TABLE 6

| | $A_i$ | $B_i$ | $C_i$ | $n(\infty)$ | $E_g$ |
|---|---|---|---|---|---|
| Vitreous | 0.0094946 | 0.0548406 | 0.0007559 | 2.863 | 0 |
| $As_2Se_3$ | 0.0054847 | 0.0248802 | 0.0001562 | | |
| Crystalline | 0.0026515 | 0.0562272 | 0.0007910 | 3.334 | 0 |
| $As_2Se_3$ | 0.0018692 | 0.0502595 | 0.0006318 | | |
| | 0.0018723 | 0.0325472 | 0.0002660 | | |
| | 0.0008620 | 0.0263903 | 0.0001742 | | |

Figure 20:
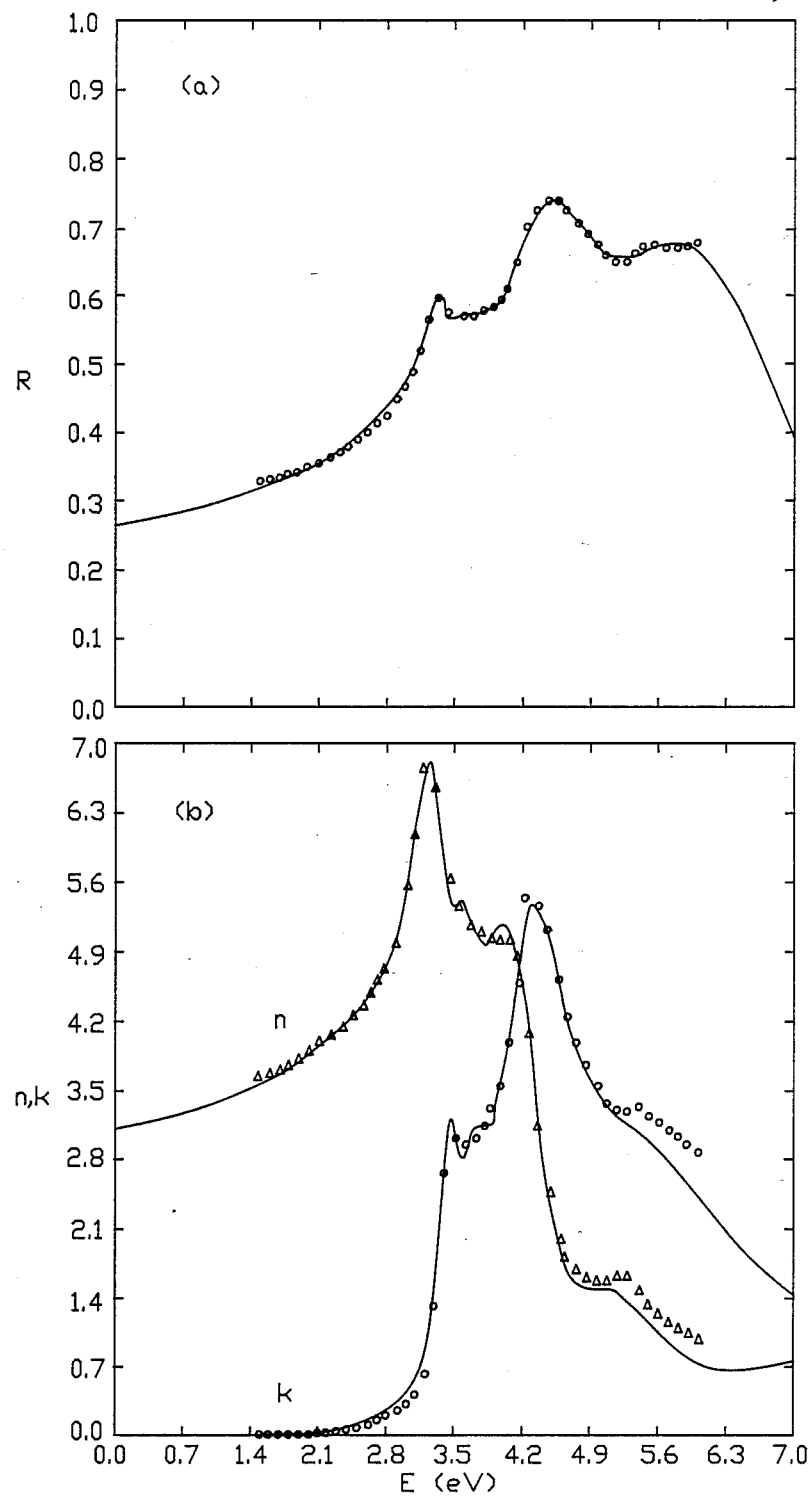
FIG. 20 shows (a) the solid line that is the theoretical plot of R(E) given by Eq.(51) with Eqs.(37) and (41) incorporated with parameters specified in Table 7 for crystalline Si. Experimental data (R:O) are taken from *Handbook of Optical Constants of Solids*; and (b) solid lines that are the n(E) and k(E) crystalline for Si determined by the above analysis (with parameters specified in Table 7) and plotted against published experimental data. Experimental data (n:Δ and k:O) are taken from *Handbook of Optical Constants of Solids*.

In Table 7, values of the parameters $A_i$, $B_i$, $C_i$, $n(\infty)$ and $E_g$ for crystalline Si obtained by least-square fitting of experimental R to Eq. (51) is equal to 4. The corresponding theoretical plot of R(E) is shown in FIG. 20(a) and the subsequent determination of n(E) and k(E) is shown in FIG. 20(b).

TABLE 7

| | $A_i$ | $B_i$ | $C_i$ | $n(\infty)$ |
|---|---|---|---|---|
| Crystalline | .00363 | 6.896 | 11.898 | 2.130 1.060 |
| Silicon | .01303 | 7.395 | 13.729 | |
| | .07736 | 8.617 | 18.754 | |
| | .11417 | 10.600 | 29.167 | | c. The Curve Fitting Program

A non-linear least-square curve-fitting computer program was used to obtain the parameters $A_i$, $B_i$ and $C_i$, and $n(\infty)$, by minimizing the sum of the square of differences of experimental and theoretical n and k simultaneously, subject to the following constraints:

$A_i$, $B_i$, $C_i$, $n(\infty)$, and $4C_i - B_i^2 > 0$.

Reasonable initial estimates of the parameters are needed in running a non-linear least-square curve-fitting program. Since k is close to a local maximum when $$\hbar\omega = [E_c(\vec{k}_{crit}) - E_v(\vec{k}_{crit})]_i$$

the position of the i-th peak in k spectrum, $E_i^{peak}$, provides an initial guess for $B_i$:

$B_i \simeq 2 E_i peak (i=1, \ldots, q)$.

It can then be shown that $C_i \simeq (E_i peak)^2 (i=1, \ldots, q)$.

An approximate value for $A_i$ can be obtained by the knowledge of the magnitude of the peaks. The initial guess for $n(\infty)$ for all materials studied was chosen as unity.

d. Results

FIGS. 9 to 16 demonstrate that Eqs. (37) and (41) describe optical properties of a large number of materials.

Each term in the sum for k in Eq. (37) contributes a peak to the k spectrum and a corresponding peak to n. In principle, the number of terms in our formulation, that is, the integer q, thus equals the number of peaks in k. In practice, however, n and k are known for a limited range of energies, in which case q is taken as the number of peaks discernable in that range. In addition, shoulders and doublets contribute to the number of terms. As an example, consider the experimentally determined optical constants of SiC in the 5-8.5 eV range as depicted in FIG. 9(a). In this range, one dominant peak in k, at 7.6 eV is present. Taking the number of terms equal to one (q=1) and $E_g$=2.5 eV, the parameters specified in Table 2 are obtained. Thus, as seen in FIG. 9(a), the optical constants of SiC in the 5-8.5 eV range are described quite well by only five parameters. Now, consider the 5-13 eV range, as depicted in FIG. 9(b). Two prominent peaks in k at 7.6 eV and 9.5 eV are present. Taking the number of terms equal to two, we then obtain the parameters specified in Table 2. The corresponding theoretical plots of n(E) and k(E) are shown in FIG. 9(b). As seen in this figure, although eight parameters give essentially all the notable features of n and k for crystalline SiC in the 5-13 eV range, a still better fit can be obtained by taking into account the shoulders at approximately 6 eV and 11 eV, that is, taking q=4. This is shown in FIG. 9(c). Therefore, as the number of terms decreases, the smaller peaks disappear and eventually only the main peak remains, resembling the amorphous state of the semiconductor.

It is seen in Table 2 that as the number of terms changes, the values of the parameters are slightly modified, as expected. However, the modifications of B and C are surprisingly small, and it is only the parameter A (which determines the strength of each term) that significantly changes.

As will be shown in the following, generally four terms are sufficient to describe n and k over a wide spectral range, indicating four dominant critical point transitions. Nevertheless, in some cases more than four terms may be required to bring out the details of the spectra.

Taking the number of terms equal to 4, corresponding to 4 "easily" discernable peaks, Table 3 contains the parameters $A_i$, $B_i$, $C_i$ and $n(\infty)$ for different materials, determined by the least-square fitting program. See FIGS. 10–12. In agreement with the previous discussion, $n(\infty)$ was found to be greater than one, the actual value depending on the material. Notice that $B_i$'s are very close to $2E_i^{peak}$. For instance, for $\alpha$-SiO$_2$, experimentally the peaks in k occur at 10.45, 11.7, 14.3, and 17.25 eV, which are very close to the $B_i/2$ values in Table 3 at 10.36, 11.64, 14.08, and 17.15 eV.

If the formulae for n and k are given, then the real and imaginary parts of the complex dielectric function are known. For example, FIG. 13(a) shows a plot of $\epsilon_2 = 2nk$ for Ge, with the parameters specified in Table 3. As seen in this figure, a much better correspondence exists between the experimental data and our formulation that the previous pseudopotential approach of Brust, Phillips, and Bassani shown in FIG. 13(b). Another example is shown in FIG. 14, depicting the excellent agreement between the present formulation and the experimental $\epsilon_1$ and $\epsilon_2$ of Si.

It appears that the reflectance spectrum provides a better guidance for determining the number of terms because structure is more readily discernable in measured R(E) than in measured k(E), since k is found experimentally from information contained in the reflectance beam. For instance, in the 0 to 27 eV range, the measured R for Ge by Phillipp and Ehrenreich contains a doublet (at ~ 2.1 and 2.3 eV), a shoulder (at ~ 3.5 eV), and two well defined peaks (at ~ 4.5 and 5.5 eV). See FIG. 16(a). Thus, taking the number of terms equal to 5 (instead of 4) should result in a better fit, bringing out the details of n and k at around 2 eV. This is seen in FIG. 15. The parameters so determined by the non-linear curve-fitting to n and k are give in Table 4. The corresponding theoretical R spectrum is plotted in FIG. 16(b), and can be compared with the measured spectrum shown in FIG. 16(a).

In FIG. 16, however, notice the poor fit between the theoretical and experimental reflectance spectra in the Vacuum UV range (E ≧ 7 eV). The reason for this is the presence of a thin "native oxide" overlayer. This is because a thin oxide, exhibiting strong absorption in the VUV range, inevitably forms on the surface of most semiconductor materials upon exposure to atmosphere, which in turn affects accurate reflectance measurements.

III. Metals

Since the uppermost valence band in metals is only partially filled, the foregoing formulation for n and k can be applied to metals by taking the energy band gap, $E_g$, contained in the semiconductor-dielectric expressions for n and k equal to zero. This gives:

$$k(E) = \sum_{i=1}^{q} A_i E^2 / (E^2 - B_i E + C_i) \quad (q = \text{integer}) \quad \text{Eq.(49)}$$

$$n(E) = n(\infty) + \sum_{i=1}^{q} (B_{0i} E + C_{0i})/(E^2 - B_i E + C_i) \quad \text{Eq.(50)}$$

where $$B_{0i} = A_i/Q_i [-(B_i^2/2) + C_i]$$

$$C_{0i} = (A_i B_i C_i)/2 Q_i$$

-continued $$Q_i = 1/2 (4C_i - B_i^2)^{1/2}$$

Example For Metals

As an example, we apply Eqs. (49) and (50) (with q=3) to the optical constants of copper. See FIG. 17. The experimental data are taken from the *Handbook of Optical Constants of Solids*. The parameters $A_i$, $B_i$, $C_i$, and $n(\infty)$ (i=1, 2, 3) describing n and k of copper are given in Table 5. We see from FIG. 17 that the theoretical carries fit the experimental data extremely well.

IV. Far Infrared Optical Constants

The foregoing formulations for optical constants also apply to the optical properties of materials in the far infrared regime.

Examples of Optical Constants in the Far Infrared

We apply Eqs. (37) and (41) to optical constants of vitreous and crystalline As$_2$Se$_3$ in the far infrared, with q=2 and 4, respectively, and $E_g=0$. The experimental data are taken from the *Handbook of Optical Constants of Solids*. The parameters $A_i$, $B_i$, $C_i$, and $n(\infty)$ (i=1, 2 for vitreous As$_2$Se$_3$, and i=1, 2, 3, 4 for crystalline As$_2$Se$_3$) describing n and k are given in Table 6. As shown in FIGS. 18 and 19, theoretical carries fit the experimental data extremely well.

Determination of Optical Constants and Film Thickness

For bulk materials, at normal incidence (zero-degree angle of incidence), the theoretical reflectance is given by $$R(E) = |\{[N_s(E) - N_a(E)]/[N_s(E) + N_a(E)]\}|^2 = \quad \text{Eq.(51)}$$

$$\{[n_s(E) - n_a(E)]^2 + [k_s(E) - k_a(E)]^2\}/\{[n_s(E) + n_a(E)]^2 + [k_s(E) + k_a(E)]^2\}$$

For a thin film of thickness d and complex index of refraction N, deposited on a substrate of known optical constants $N_s$, the normal-incidence reflectance at wavelength g is given by $$R(E) = \left| \frac{r_{12} + r_{23}\exp(-i\delta)}{1 + r_{12}r_{23}\exp(-i\delta)} \right|^2 \quad \text{Eq.(52)}$$

where $$r_{12} = [N(E) - N_a(E)]/[N(E) + N_a(E)]$$

$$r_{23} = [N_s(E) - N(E)]/[N_s(E) + N(E)]$$

and $$\delta = (4\pi d/\tau)N(E).$$

The formulae for reflectance at an angle of incidence different from zero, as well as perpendicular and parallel polarization, for bulk and multilayer thin films can be found in O.S. Heavens, "*Optical Properties of Thin Solid Films*" (Butterworth, London, 1955).

Thus, the parameters describing the spectral dependence of N as well as the film thickness can be obtained by minimizing the difference between the measured and theoretical reflectance spectra.

Example of Determination of Optical Constants From Reflectance

As an example, we apply Eq. (51) for R, with Eqs. (37) and (41) incorporated to the case of crystalline silicon. The experimental data are taken from the *Handbook of Optical Constants of Solids*. The parameters $A_i$, $B_i$, $C_i$, $n(\infty)$, and $E_g$ (i=1, 2, 3, 4), presented in Table 7, are determined by a least-square fitting of the experimental data to be theoretical expression of reflectance, thus yielding n(E) and k(E). See FIG. 20.

When the value of the thickness, d, is to be utilized in connection with determining optical properties of materials, Eq. (52) is utilized in combination with Eqs. (37) and (41). Specifically, the value of R of Eq. (52) is used to determine the calculated output signals. Note that in Eq. (52), the values are $R_{12}$ and $R_{23}$ employ the calculated complex index of refraction, $N_a$, determined in accordance with Eqs. (37) and (41). When Eq. (52) is employed, an initial estimate of the thickness, d, is utilized. The initial estimate can be any value.

Figure 21:
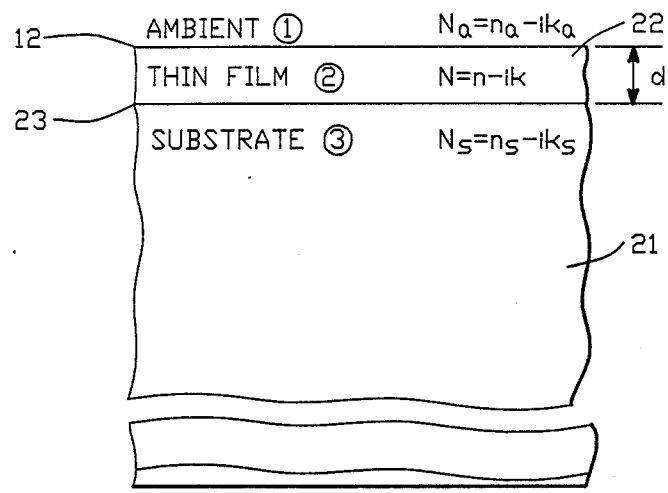
FIG. 21 depicts a representation of a thin film material supported by a substrate which is analyzed in accordance with the present invention.

Referring to FIG. 21, a substrate material 21 carries a thin film 22. The region above the thin film 22 is the ambient environment in which an incident input beam is to be directed at the thin film 22 in the underlying substrate 21. The ambient region is referred to with a subscript of 1, the thin film region is referred to with a subscript 2, and the substrate is referred to with a subscript 3. The fresnel coefficient for the interface 12 is designated as $R_{12}$. The fresnel coefficient for the interface 23 between the thin film 22 and the substrate 21 is desginated as $R_{23}$. The ratio of the intensity of the input beam and the reflected beam for the composite material of FIG. 21 is designated as R. The value of R is dependent upon the complex index of refraction, N, of the thin film material 22 and of the complex index of refraction $N_s$ of the substrate 21 as well as by the thickness, d, of the thin film material 22. The relationship between the ratio, R, the complex index of refraction, N, and the thickness of the film is given by the following Eq. (52).

Figure 22:
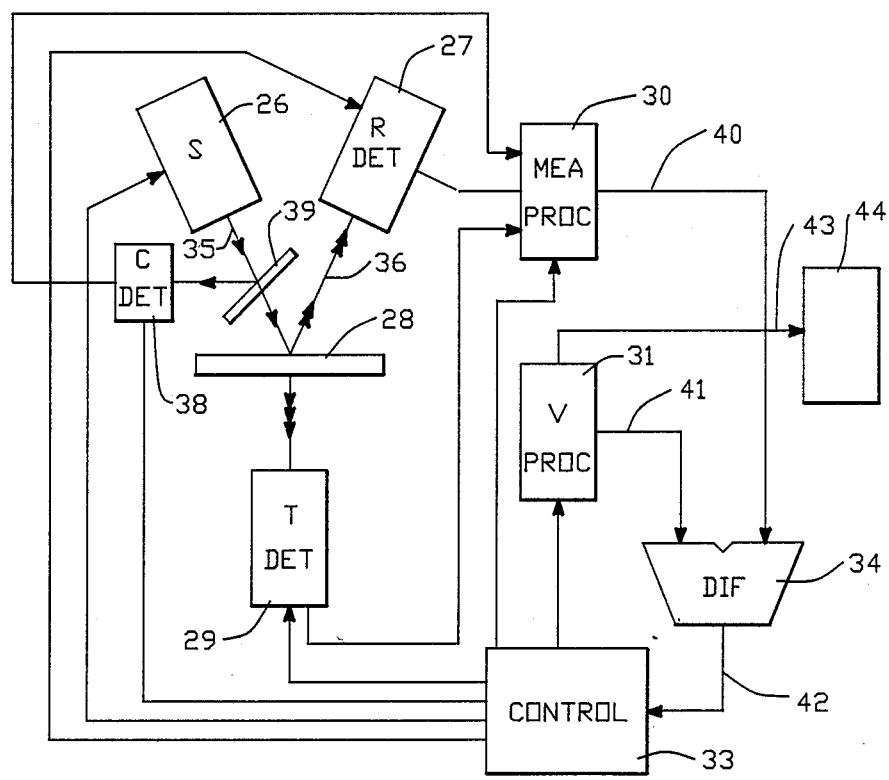
FIG. 22 shows a block diagram of the apparatus of the present invention.

If in FIG. 21 additional thin film layers exist between the thin film 22 and the substrate 21, then the substrate 21, for purposes of this explanation, is considered to include a composite complex index of refraction $N_s$ which is applicable for the substrate and any intermediate thin film layers which exist. In FIG. 22, an apparatus which operates in accordance with the methods of the present invention is shown. A light source 26 operates to provide an input beam 35 incident on the material to be tested 28. The incident beam 35 results in a reflected beam 36 and a transmitted beam 37. The source 26 is controllable to have a different range of frequencies in its output beam 35 under the control of control 33. The frequency range extends over any portion of the spectrum from the far infrared through visible to the far ultraviolet. The frequency spectrum, the input spectrum of the input beam 35, causes the frequency spectrum of the reflected beam 36 to be the same and the frequency spectrum of the transmitted beam 37 to be the same. The reflected beam 36 is detected by a reflection detector 27. Detector 27 is controlled by control 33 to be operative over the same frequency range as the frequency range determined by the source 26.

The transmitted beam 37, when present, is detected by the transmission detector 29. Transmission detector 29 is controlled by control 33 to be operative over the same frequency spectrum as that controlled for the source 26. A calibration detector 38 is provided for sensing the input beam 35 from the beam splitter 39. The calibration detector 38 provides the measure of the intensity of the input beam to the measurement processor 30. Similarly, the reflection detector 27 provides the measurement of the intensity of the reflected beam to the processor 30 and the transmission detector 29 provides a measure of the intensity of the transmitted beam to the measure processor 30. The measurement processor forms the measured value of the ratio of the input beam intensity to the output beam (either reflected or transmitted) to provided measured beam signals on electrical bus 40. The measured beam signals are input to the comparator 34.

In FIG. 22, a value processor 31 provides the calculated value of the ratio signal on bus 41 which are input to the comparator 34. The comparator 34 compares the measured value signals with the calculated value signals and provides a comparison value on bus 42 which is input to the control 33. Control 33 can accept the difference value on bus 42 if the difference between the measured value and the calculated value is small enough. Alternatively, in typical applications, control 33 signals the value processor 31 to modify one or more of the control values A, B, C, $n(\infty)$, or thickness, d, and causes the difference between the measured and calculated values again to be compared in different circuit 34. In a typical operation, 100 iterations of modification of calculated values occur before the calculated values in the value processor 31 are acceptable. Any standard curve fitting program may be employed in selecting the manner and the amounts at which the variables are modified during each pass of the iteration. While 100 iterations are typcial, of course, a single iteration or many times a 100 iterations are well within the contemplated operation. After each iteration or the final iteration, the optical properties are output on bus 43 to a display or other output device 44.

What is claimed is:

1. A method of determining the optical properties of a material by means of an optical instrument and data processor means, comprising:

providing in said instrument an input beam, having a plurality of frequencies where each frequency has an associated photon energy and an input intensity, said input beam incident upon said material and interacting with said material to provide an output beam, said output beam having said plurality of frequencies where each frequency has an associated photon energy and has an output intensity, said material having electrons transferring from an initial state to a final state as a result of interaction with said input beam;

measuring in said instrument the output intensities of said output beam for said frequencies to form measured output signals proportional to the output intensities at said frequencies;

calculating in said data processor means a calculated complex index of refraction for said material as a function of energy and of a probability term related to the probability that an electron transition will occur from the initial state to the final state for the material, an energy term related to the difference in energy between the initial state and the final state for the material, a life-time term related to the life-time that electrons tend to remain in the final state for the material;

processing in said data processor means said calculated complex index of refraction to form calculated output signals, comparing said calculated output signals with said measured output signals to determine difference signals proportional to the difference between said measured output signals and said calculated output signals.

2. The method of claim 1 wherein said output beam is a transmitted beam.

3. The method of claim 1 wherein said output beam is a reflected beam.

4. The method of claim 1 wherein said processing step uses a value of the thickness of said material together with said complex index of refraction to form said calculated output signals.

5. The method of claim 4 wherein said calculating step uses $$R(E) = |\{[N_s(E) - N_a(E)]/[N_s(E) + N_a(E)]\}|^2 =$$
$$\{[n_s(E) - n_a(E)]^2 + [k_s(E) - k_a(E)]^2\}/\{[n_s(E) + n_a(E)]^2 + [k_s(E) + k_a(E)]^2\}$$

where $N_a$ is the complex index of refraction of ambient for a thin film of thickness d and complex index of refraction N, deposited on a substrate of known optical constants $N_s$, with the normal-incidence reflectance at wavelength $\lambda$ is given by $$R(E) = \left| \frac{r_{12} + r_{23}\exp(-i\delta)}{1 + r_{12}r_{23}\exp(-i\delta)} \right|^2$$

where $$r_{12} = [N(E) - N_a(E)]/[N(E) + N_a(E)]$$
$$r_{23} = [N_s(E) - N(E)]/[N_s(E) + N(E)]$$

and $$\delta = (4\pi d/\lambda)N(E).$$

For $d = 0$, $$R(E) = |\{[N_s(E) - N_a(E)]/[N_s(E) + N_a(E)]\}|^2 =$$
$$\{[n_s(E) - n_a(E)]^2 + [k_s(E) - k_a(E)]^2\}/\{[n_s(E) + n_a(E)]^2 + [k_s(E) + k_a(E)]^2\}.$$

6. The method of claim 1 wherein said processing step uses a value of $E_g$ for said material together with said complex index of refraction to form said calculated output signals.

7. The method of claim 1 wherein,
said measuring step measures the ratio of the input intensity and the output intensity for said frequencies whereby the ratio has at least one maximum value, Rpeak, at a corresponding value of energy, E(Rpeak); and
said probability term is determined from Rpeak,
said energy term is determined from E(Rpeak),
said life-time term is determined from E(Rpeak).

8. The method of claim 1 wherein said calculating step, said processing step and said comparing step are iteratively repeated and wherein for each iteration, one or more of said probability, energy and lifetime terms is changed whereby a changed calculated complex index of refraction for said material is formed and said processing step responsively forms changed calculated output signals, and wherein said changed calculated output signals are compared with said measured output signals to provide changed difference signals.

9. The method of claim 8 wherein
said measuring step measures the ratio of the input intensity and the output intensity for said frequencies whereby the ratio has at least one maximum value, Rpeak, at a corresponding value of energy, E(Rpeak); and
said probability term is determined from Rpeak,
said energy term is determined from E(Rpeak),
said life-time term is determined from E(Rpeak).

10. The method of claim 8 wherein said processing step uses a value of the thickness of said material together with said complex index of refraction to form said calculated value.

11. The apparatus of claim 1 wherein said output beam is a transmitted beam.

12. The apparatus of claim 1 wherein said output beam is a reflected beam.

13. The apparatus of claim 1 wherein said processor means uses a value of the thickness of said material together with said complex index of refraction to form said calculated value.

14. The apparatus of claim 1 wherein said processor means uses a value of $E_g$ for said material together with said complex index of refraction to form said calculated value.

15. The apparatus of claim 1 wherein said input beam has an input range of frequencies and wherein said output beam has an output range of frequencies equal to said input range.

16. The apparatus of claim 1 wherein,
said means for measuring the ratio of the input intensity and the output intensity for said frequencies whereby the ratio has at least one maximum value, Rpeak, at a corresponding value of energy, E(Rpeak); and
said probability term is determined from Rpeak,
said energy term is determined from E(Rpeak),
said life-time term is determined from E(Rpeak).

17. An apparatus for determining the optical properties of a material comprising:
optical instrument means for providing an input beam having a plurality of frequencies where each frequency has an associated photon energy and an input intensity, incident upon said material and interacting with said material to provide an output beam, said output beam having said plurality of frequencies where each frequency has an associated photon energy and has an output intensity, said material having electrons transferring from an initial state to a final state as a result of interaction with said input beam;
means for measuring the output intensities of said output beam for said frequencies to form measured output signals proportional to the output intensities at said frequencies;
processor means for forming calculated output signals representing a complex index of refraction for said material as a function of energy and as a function of
a probability term related to the probability that an electron transition will occur from the initial state to the final state for the material, an energy term related to the difference in energy between the initial state and the final state for the material, a life-time term related to the life-time that electrons tend to remain in the final state for the material;

means for comparing said calculated output signals with said measured output signals to determine difference signals proportional to the difference between said measured output signals and said calculated output signals.

18. A method of determining the optical properties of a material over a range of frequencies by means of an optical instrument and data processor means, comprising:

providing in said instrument an input beam, having a plurality of frequencies not coextensive with said range of frequencies where each frequency has an associated photon energy and an input intensity, incident upon said material and interacting with said material to provide an output beam, said output beam having said plurality of frequencies where each frequency has an associated photon energy and has an output intensity, said material having electrons transferring from an initial state to a final state as a result of interaction with said input beam;

measuring in said instrument the ratio of the input intensity and the output intensity for said frequencies whereby the ratio has at least one maximum value, Rpeak, at a corresponding value of energy, E(Rpeak);

determining in said processor means the complex index of refraction of said material over said range of frequencies as a function of energy and of a probability term determined from Rpeak and related to the probability that an electron transition will occur from the initial state to the final state for the material, an energy term determined from E(Rpeak) and related to the difference in energy between the initial state and the final state for the material, a life-time term determined from E(Rpeak) and related to the life-time that electrons tend to remain in the final state for the material.

19. A method of determining the optical properties of a material by means of an instrument connected to data processor means, comprising:

providing in said instrument an input beam, having a plurality of frequencies where each frequency has an associated photon energy, E, and an input intensity, incident upon said material and interacting with said material to provide an output beam, said output beam having said plurality of frequencies where each frequency has an associated photon energy and has an output intensity, said material having electrons transferring from an initial state to a final state as a result of interaction with said input beam;

measuring in said instrument the ratio, R, of the input intensity and the output intensity for said frequencies of energy, E, whereby the ratio has at least one maximum value, Rpeak, at a corresponding value of energy, E(Rpeak);

determining in said processor means the complex index of refraction, N(E), of said material as a function of energy where N(E), equals n(E)-ik(E) and where n(E) is the refractive index, k(E) is the extinction coefficient and i is $(-1)^{\frac{1}{2}}$ as follows, $$n(E) = n(\infty) + \frac{B_0 E + C_0}{E^2 - BE + C},$$

$$k(E) = \frac{AE^2}{E^2 - BE + C},$$

where A is a probability term determined from Rpeak and related to the probability that an electron transition will occur from the initial state to the final state for the material, where B is an energy term determined from E(Rpeak) and related to the difference in energy between the initial state and the final state for the material, where C is a life-time term determined from E(Rpeak) and related to the life-time that electrons tend to remain in the final state for the material, and where, $$Q = (1/2)(4C - B^2)^{1/2},$$

$$B_0 = (A/Q)(-B^2/2 + C)$$

$$C_0 = ABC/2Q$$

$n(\infty) = n(E)$ as $E$ approaches $\infty$.

20. A method of determining the optical properties of a material over a range of frequencies by means of an optical instrument and data processor means, comprising:

providing in said instrument an input beam, having a plurality of frequencies not extending over said range of frequencies where each frequency has an associated photon energy, E, and an input intensity, incident upon said material and interacting with said material to provide an output beam, said output beam having said plurality of frequencies where each frequency has an associated photon energy and has an output intensity, said material having electrons transferring from an initial state to a final state as a result of interaction with said input beam;

measuring in said optical instrument the ratio, R, of the input intensity and the output intensity for said plurality of frequencies of energy, E, whereby the ratio has at least one maximum value, Rpeak, at a corresponding value of energy, E(Rpeak);

determining in said processor means the complex index of refraction, N(E), of said material for said range of frequencies as a function of energy where N(E) equals n(E)-ik(E) and where n(E) is the refractive index, k(E) is the extinction coefficient and i is $(-1)^{178}$ as follows, $$n(E) = n(\infty) + \frac{B_0 E + C_0}{E^2 - BE + C}$$

$$k(E) = \frac{A(E - E_g)^2}{E^2 - BE + C},$$

where A is a probability term determined from Rpeak and related to the probability that an electron transition will occur from the initial state to the final state for the material, where B is an energy term determined from E(Rpeak) and related to the difference in energy between the initial state and the final state for the material, where C is a life-time term determined from E(Rpeak) and related to the life-time that electrons tend to remain in the final state for the material, and where, $$Q = (1/2) (4C - B^2)^{1/2},$$

$$B_0 = (A/Q)[-(B^2/2) + E_g B - E_g^2 + C],$$

$$C_0 = (A/Q)[(E_g^2 + C)(B/2) - 2E_g C],$$

$n(\infty) = n(E)$ as $E$ approaches $\infty$.

21. A method of determining the optical properties of a material by means of an optical instrument and data processor means, comprising:

providing in said instrument an input beam, having a plurality of frequencies where each frequency has an associated photon energy, E, and an input intensity, incident upon said material and interacting with said material to provide an output beam, said output beam having said plurality of frequencies where each frequency has an associated photon energy and has an output intensity, said material having electrons transferring from an initial state to a final state as a result of interaction with said input beam;

measuring in said instrument the ratio, R, of the input intensity and the output intensity for said frequencies of energy, E, whereby the ratio has at least one maximum value, Rpeak, at a corresponding value of energy, E(Rpeak);

determining in said processor means the complex index of refraction, N(E), of said material as a function of photon energy where N(E) equals n(E)-ik(E) and where n(E) is the refractive index, k(E) is the extinction coefficient and i is $(-1)^{\frac{1}{2}}$ as follows, $$n(E) = n(\infty) + \sum_{i=1}^{q} \frac{B_{0i}E + C_{0i}}{E^2 - B_i E + C_i}, \quad q = \text{number of peaks}$$

$$k(E) = \sum_{i=1}^{q} \frac{A_i E^2}{E^2 - B_i E + C_i},$$

where A is a probability term determined from Rpeak and related to the probability that an electron transition will occur from the initial state to the final state for the material, where B is an energy term determined from E(Rpeak) and related to the difference in energy between the initial state and the final state for the material, where C is a life-time term determined from E(Rpeak) and related to the life-time that electrons tend to remain in the final state for the material, and where, $$Q_i = (1/2) (4C_i - B_i^2)^{1/2},$$

$$B_{0i} = (A_i/Q_i) (-B_i^2/2 + C_i)$$

$$C_{0i} = A_i B_i C_i / 2 Q_i$$

$n(\infty) = n(E)$ as $E$ approaches $\infty$.

22. A method of determining the optical properties of a material by means of an optical instrument and data processor means, comprising:

providing in said instrument an input beam, having a plurality of frequencies where each frequency has an associated photon energy, E, and an input intensity, incident upon said material and interacting with said material to provide an output beam, said output beam having said plurality of frequencies where each frequency has an associated photon energy and has an output intensity, said material having electrons transferring from an initial state to a final state as a result of interaction with said input beam;

measuring in said instrument the ratio, R, of the input intensity and the output intensity for said frequencies of energy, E, whereby the ratio has at least one maximum value, Rpeak, at a corresponding value of energy, E(Rpeak);

determining in said processor means the complex index of refraction, N(E), of said material as a function of photon energy where N(E) equals n(E)-ik(E) and where n(E) is the refractive index, k(E) is the extinction coefficient and i is $(-1)^{\frac{1}{2}}$ as follows, $$k(E) = \left( \sum_{i=1}^{q} \frac{A_i}{E^2 - B_i E + C_i} \right)(E - E_g)^2 \quad (q = \text{integer})$$

$$n(E) = n(\infty) + \sum_{i=1}^{q} \frac{B_{0i} E + C_{0i}}{E^2 - B_i E + C_i} \quad (q = \text{integer})$$

where A is a probability term determined from Rpeak and related to the probability that an electron transition will occur from the initial state to the final state for the material, where B is an energy term determined from E(Rpeak) and related to the difference in energy between the initial state and the final state for the material, where C is a life-time term determined from E(Rpeak) and related to the life-time that electrons tend to remain in the final state for the material, and where, $$B_{0i} = (A_i/Q_i)\{-(B_i^2/2) + E_g B_i - E_g^2 + C_i\}$$

$$C_{0i} = (A_i/Q_i)\{(E_g^2 + C_i)(B_i/2) - 2E_g C_i\}$$

$$Q_i = (1/2) (4C_i - B_i^2)^{1/2}$$

$n(\infty) = n(E)$ as $E$ approaches $\infty$.

23. An apparatus for determining the optical properties of a material over a range of frequencies comprising:

optical instrument means for providing an input beam, having a plurality of frequencies not extending over said range of frequencies where each frequency has an associated photon energy, E, and an input intensity, incident upon said material and interacting with said material to provide an output beam, said output beam having said plurality of frequencies where each frequency has an associated photon energy and has an output intensity, said material having electrons transferring from an initial state to a final state as a result of interaction with said input beam;

said instrument including means for measuring the ratio, R, of the input intensity and the output intensity for said plurality of frequencies of energy, E, whereby the ratio has at least one maximum value, Rpeak, at a corresponding value of energy, E(Rpeak);

processor means for determining the complex index of refraction, N(E), of said material for said range of frequencies as a function of energy where N(E) equals n(E)-ik(E) and where n(E) is the refractive index, k(E) is the extinction coefficient and i is $(-1)^{\frac{1}{2}}$ as follows, $$n(E) = n(\infty) + \frac{B_0 E + C_0}{E^2 - BE + C}$$

-continued $$k(E) = \frac{A(E - E_g)^2}{E^2 - BE + C},$$

where A is a probability term determined from Rpeak and related to the probability that an electron transition will occur from the initial state to the final state for the material, where B is an energy term determined from E(Rpeak) and related to the difference in energy between the initial state and the final state for the material, where C is a life-time term determined from E(Rpeak) and related to the life-time that electrons tend to remain in the final state for the material, and where, $$Q = (1/2)(4C - B^2)^{1/2},$$

$$B_0 = (A/Q)[-(B^2/2) + E_g B - E_g^2 + C],$$

$$C_0 = (A/Q)[(E_g^2 + C)(B/2) - 2E_g C],$$

$$n(\infty) = n(E) \text{ as } E \text{ approaches } \infty.$$

* * * * *